(12) United States Patent
Escalante et al.

(10) Patent No.: US 9,678,071 B2
(45) Date of Patent: Jun. 13, 2017

(54) DETECTING LATENT TUBERCULOSIS INFECTIONS

(71) Applicant: Mayo Foundation for Medical Education and Research, Rochester, MN (US)

(72) Inventors: Patricio Escalante, Rochester, MN (US); Keith L. Knutson, Rochester, MN (US); Tobias Peikert, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 17 days.

(21) Appl. No.: 14/371,371

(22) PCT Filed: Jan. 8, 2013

(86) PCT No.: PCT/US2013/020688
§ 371 (c)(1),
(2) Date: Jul. 9, 2014

(87) PCT Pub. No.: WO2013/106338
PCT Pub. Date: Jul. 18, 2013

(65) Prior Publication Data
US 2015/0010927 A1  Jan. 8, 2015

Related U.S. Application Data

(60) Provisional application No. 61/586,019, filed on Jan. 12, 2012.

(51) Int. Cl.
*A61K 39/04* (2006.01)
*A61K 38/10* (2006.01)
*A61K 38/16* (2006.01)
*A61K 39/44* (2006.01)
*G01N 33/569* (2006.01)
*C12Q 1/04* (2006.01)

(52) U.S. Cl.
CPC ......... *G01N 33/56911* (2013.01); *C12Q 1/04* (2013.01); *G01N 33/5695* (2013.01)

(58) Field of Classification Search
CPC .......... A61K 38/10; A61K 2039/55516; A61K 39/04; A61K 38/16; C12N 5/0636; C12N 2501/599; C07K 14/70521; C07K 14/70596; G01N 33/505; G01N 33/5047; G01N 2500/10; G01N 33/6866; G01N 33/5695
See application file for complete search history.

(56) References Cited

U.S. PATENT DOCUMENTS

| | | | |
|---|---|---|---|
| 4,208,479 A * | 6/1980 | Zuk | C07J 41/0016 435/7.72 |
| 7,572,597 B2 | 8/2009 | Lalvani et al. | |
| 7,575,870 B1 | 8/2009 | Lalvani et al. | |
| 7,608,392 B2 | 10/2009 | Rothel et al. | |
| 7,785,607 B2 | 8/2010 | Goletti et al. | |
| 8,030,005 B2 | 10/2011 | Kelleher et al. | |
| 2005/0074822 A1 * | 4/2005 | Nixon | G01N 33/505 435/7.2 |
| 2006/0002941 A1 * | 1/2006 | Mahairas | A61K 39/00 424/178.1 |
| 2009/0221005 A1 | 9/2009 | Kelleher et al. | |
| 2014/0323333 A1 | 10/2014 | Escalante et al. | |

FOREIGN PATENT DOCUMENTS

WO  WO 2011/113953  9/2011

OTHER PUBLICATIONS

Restrepo et al., (Clinical infection disease 2008;47:634-41).*
Laurens et al., (Clinical and Diagnostic Laboratory Immunology, Mar. 2000, p. 155-160).*
OptEIA BD Biosciences,2010,(retrieved from http://www.bdbiosciences.com/ptProduct.jsp?ccn=555142).*
OptEIA BD Biosciences catalog 2010 retrieved from https://static.fishersci.com/cmsassets/downloads/segment/Scientific/pdf/bd_elisa_elispot_product_list.pdf.*
Sester et al., "Tuberculin skin testing underestimates a high prevalence of latent tuberculosis infection in hemodialysis patients," *Kidney Int.*, 65(5):1826-1834, May 2004.
Sutherland et al., "Pattern and diversity of cytokine production differentiates between *Mycobacterium tuberculosis* infection and disease," *Eur J Immunol*, 39(3):723-729, Mar. 2009.
van Zyl-Smith, "Within-subject variability and boosting of T-cell interferon-gamma responses after tuberculin skin testing," *Am J Respir Crit Care Med.*, 180(1):49-58, Epub Apr. 2, 2009.
Waldrolp et al., "Normal human CD4+ memory T cells display broad heterogeneity in their activation threshold for cytokine synthesis," *J Immunol.*, 161(10):5284-5295, Nov. 15, 1998.
Watts et al., "T cell costimulatory molecules in anti-viral immunity. Potential role in immunotherapeutic vaccines," *Can J Infect Dis*, 14(4):221-229, Jul. 2003.
Zaunders et al., "High levels of human antigen-specific CD4+ T cells in peripheral blood revealed by stimulated coexpression of CD25 and CD134 (OX40)," *J Immunol.*, 183(4):2827-2836, Epub Jul. 27, 2009.
International Search Report and Written Opinion for PCT/US2013/020688, mailed Apr. 11, 2013, 6 pages.
International Preliminary Report on Patentability for PCT/US2013/020688, mailed Jul. 24, 2014, 6 pages.
Ravn et al., "Human T cell responses to the ESAT-6 antigen from *Mycobacterium tuberculosis*," J Infect Dis., 179 (3):637-645, Mar. 1999.
Smith et al., "Human CD8(+) T cells specific for *Mycobacterium tuberculosis* secreted antigens in tuberculosis patients and healthy BCG-vaccinated controls in the Gambia," Infect Immun., 68(12):7144-7148, Dec. 2000.

(Continued)

*Primary Examiner* — Shafiqul Haq
*Assistant Examiner* — Carmencita M Belei
(74) *Attorney, Agent, or Firm* — Fish & Richardson P.C.

(57) ABSTRACT

This document provides methods and materials related to identifying mammals having a LTBI. For example, methods and materials for using ELISpot assays to identify mammals (e.g., humans) having a LTBI are provided.

1 Claim, 38 Drawing Sheets

(56) References Cited

OTHER PUBLICATIONS

Escalante et al., "Combinatorial Immunoprofiling in Latent Tuberculosis Infection: Toward Better Risk Stratification," *Am J Respir Crit Care Med.*, 192(5):605-617, Epub. Jun. 1, 2015.

Sadler et al., "Establishment of a healthy human range for the whole blood "OX40" assay for the detection of antigen-specific CD4+ T cells by flow cytometry," *Cytometry B Clin Cytom.*, 86(5):350-361, Epub May 14, 2014.

Arend et al., "Antigenic equivalence of human T-cell responses to *Mycobacterium tuberculosis*-specific RD1-encoded protein antigens ESAT-6 and culture filtrate protein 10 and to mixtures of synthetic peptides," *Infect Immun.*, 68(6):3314-3321, Jun. 2000.

Berry, "An interferon-inducible neutrophil-driven blood transcriptional signature in human tuberculosis," *Nature*, 466(7309):973-977, Aug. 19, 2010.

Butera et al., "New tools for detecting latent tuberculosis infection: evaluation of RD1-specific long-term response," *BMC Infect Dis*, 9:182, Nov. 21, 2009.

Casey et al., "Enumeration of functional T-cell subsets by fluorescence-immunospot defines signatures of pathogen burden in tuberculosis," *PLoS One*, 5(12):e15619; 11 pages, Dec. 14, 2010.

Dinser et al., "Evaluation of latent tuberculosis infection in patients with inflammatory arthropathies before treatment with TNF-alpha blocking drugs using a novel flow-cytometric interferon-gamma release assay," *Rheumatology (Oxford).*, 47(2):212-218, Feb. 2008.

Einarsdottir et al., "Cytotoxicity and secretion of gamma interferon are carried out by distinct CD8 T cells during *Mycobacterium tuberculosis* infection," *Infect Immun.*, 77(10):4621-4630, Epub Aug. 10, 2009.

Escalante et al., "Evaluation of a novel flow cytometric method for the diagnosis of latent tuberculosis infection," ATS International Conference, San Francisco, May 22, 2012, 33 pages [slideshow].

Escalante et al., [Poster Board # B89] "Evaluation of a novel flow cytometric for the diagnosis of latent tuberculosis infection," C61. Immunodiagnostics Latent Tuberculosis Infection and Tuberculosis., *Am J Respir Crit Care Med.*, 185:2012:A4722, May 1, 2012.

Escalante, "Pilot study of latent tuberculosis infection with an enhanced elispot interferon-gamma release assay (TB-Elispot)," 3rd Global Symposium on IGRAs 2012 [slideshow], Retreived from the Internet <URL: https://cme.ucsd.edu/igras/syllabus/sun/845a-Escalante-sun.pdf>, Jan. 12-15, 2012, 20 pages.

Ferrara et al., "Use in routine clinical practice of two commercial blood tests for diagnosis of infection with *Mycobacterium tuberculosis*: a prospective study," *Lancet*, 367(9519):1328-1334, Apr. 22, 2006.

Feske et al., "Enhancement of human antigen-specific memory T-cell responses by interleukin-7 may improve accuracy in diagnosing tuberculosis," *Clin Vaccine Immunol.*, 15(10):1616-1622, Epub Aug. 27, 2008.

Hsu et al., "A novel assay detecting recall response to *Mycobacterium tuberculosis*: Comparison with existing assays," *Tuberculosis (Edinb).*, 92(4):321-327, Epub Apr. 26, 2012.

Lasiglie et al., "Analysis of IL 23/IL 17 axis in patients carrying cias-1/Nalp3 gene mutation, further evidences of IL-1B influence in development of $T_H17$ cells in humans," *Eur. J. Immunol.*, p. S 596, Abstract WSC20/4, 1 page, Wednesday, Workshop, 2009.

Marin et al., "Regulatory T cell frequency and modulation of IFN-gamma and IL-17 in active and latent tuberculosis," *Tuberculosis (Edinb).*, 90(4):252-261, Epub Jul. 1, 2010.

Menzies et al., "Meta-analysis: new tests for the diagnosis of latent tuberculosis infection: areas of uncertainty and recommendations for research," *Ann Intern Med.*, 146(5):340-354, Mar. 6, 2007.

Ott et al., "CD28 costimulation enhances the sensitivity of the ELISPOT assay for detection of antigen-specific memory effector CD4 and CD8 cell populations in human diseases," *J Immunol Methods.*, 285(2):223-235, Feb. 15, 2004.

Pollock et al., "Discordant QuantiFERON-TB Gold test results among US healthcare workers with increased risk of latent tuberculosis infection: a problem or solution?" *Infect Control Hosp Epidemiol.*, 29(9):878-886, Sep. 2008.

Sester et al., "Improved efficiency in detecting cellular immunity towards *M. tuberculosis* in patients receiving immunosuppressive drug therapy," *Nephrol Dial Transplant.*, 21(11):3258-3268, Epub Aug. 25, 2006.

\* cited by examiner (*) Wilcoxon (Rank sum test)

TB_ELISPOT (52.33 cut off)

Contingency Table

| Count<br>Row % | 0 | 1 | |
|---|---|---|---|
| Normal Donor | 17<br>100.00 | 0<br>0.00 | 17 |
| Remote TB | 0<br>0.00 | 2<br>100.00 | 2 |
| Active TB | 1<br>50.00 | 1<br>50.00 | 2 |
| Prob LTBI (TST+/IGRA+ or TSTconv) | 1<br>11.11 | 8<br>88.89 | 9 |
| Poss LTBI (TST+/IGRA- or TST-/IGRA-) | 1<br>33.33 | 2<br>66.67 | 3 |
| | 20 | 13 | 33 |

Fig. 14

TB_ELISPOT (52.33 cut off)

Contingency Table

| TB contact likelihood | Count / Row % | 0 | 1 | |
|---|---|---|---|---|
| | Active TB, old TB, definitive TB contact | 1 | 4 | 5 |
| | | 20.00 | 80.00 | |
| | Probable TB contact | 7 | 9 | 16 |
| | | 43.75 | 56.25 | |
| | Possible TB contact | 5 | 0 | 5 |
| | | 100.00 | 0.00 | |
| | Unlikely TB contact | 7 | 0 | 7 |
| | | 100.00 | 0.00 | |
| | | 20 | 13 | 33 |

Fig. 15

SEQUENCE LISTING

```
<160> NUMBER OF SEQ ID NOS: 6

<210> SEQ ID NO 1
<211> LENGTH: 20
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala Ser
 1               5                  10                  15

Ala Ile Gln Gly
            20

<210> SEQ ID NO 2
<211> LENGTH: 20
<212> TYPE: PRT
<213> ORGANISM: Mycobacterium tuberculosis

<400> SEQUENCE: 2

Glu Gly Lys Gln Ser Leu Thr Lys Leu Ala Ala Ala Trp Gly Gly Ser
 1               5                  10                  15

Gly Ser Glu Ala
            20

<210> SEQ ID NO 3
<211> LENGTH: 24
<212> TYPE: PRT
<213> ORGANISM: Mycobacterium tuberculosis

<400> SEQUENCE: 3

Ala Trp Gly Gly Ser Gly Ser Glu Ala Tyr Gln Gly Val Gln Gln Lys
 1               5                  10                  15

Trp Asp Ala Thr Ala Thr Glu Leu
            20

<210> SEQ ID NO 4
<211> LENGTH: 20
<212> TYPE: PRT
<213> ORGANISM: Mycobacterium tuberculosis

<400> SEQUENCE: 4

Thr Ala Thr Glu Leu Asn Asn Ala Leu Gln Asn Leu Ala Arg Thr Ile
 1               5                  10                  15
```

```
Ser Glu Ala Gly
        20

<210> SEQ ID NO 5
<211> LENGTH: 20
<212> TYPE: PRT
<213> ORGANISM: Mycobacterium tuberculosis

<400> SEQUENCE: 5

Ala Gln Ala Ala Val Val Arg Phe Gln Glu Ala Ala Asn Lys Gln Lys
 1               5                  10                  15

Gln Glu Leu Asp
        20

<210> SEQ ID NO 6
<211> LENGTH: 20
<212> TYPE: PRT
<213> ORGANISM: Mycobacterium tuberculosis

<400> SEQUENCE: 6

Glu Ile Ser Thr Asn Ile Arg Gln Ala Gly Val Gln Tyr Ser Arg Ala
 1               5                  10                  15

Asp Glu Glu Gln
        20
```

DETECTING LATENT TUBERCULOSIS INFECTIONS

CROSS-REFERENCE TO RELATED APPLICATIONS

This application is a National Stage application under 35 U.S.C. 371 of International Application No. PCT/US2013/020688, having an International Filing Date of Jan. 8, 2013, which claims the benefit of priority to U.S. Provisional Application Ser. No. 61/586,019, filed on Jan. 12, 2012. The disclosure of the prior application is considered part of (and is incorporated by reference in) the disclosure of this application.

BACKGROUND

1. Technical Field

This document relates to methods and materials involved in identifying mammals having a latent tuberculosis infection (LTBI). For example, this document relates to methods and materials for using enzyme-linked immunosorbent spot (abbreviated herein as ELISpot, Elispot, or ELISPOT) assays to identify mammals having a LTBI.

2. Background Information

Tuberculosis (TB) is important because it disproportionately affects minorities and immigrants in the United States and vast populations around the world. Accurate detection of LTBI continues to be challenging, and undiagnosed LTBI patients can progress to active TB disease with potentially devastating consequences. Interpretation of discordant testing (e.g., tuberculin skin tests (TST) and interferon-gamma release assays (IGRA) in LTBI also can be a significant problem. Both TST and IGRA tests usually detect T-cell activation against *Mycobacterium tuberculosis*, but they do not appear to differentiate patients with dormant forms of TB infection from the ones who have cleared their infections.

SUMMARY

This document provides methods and materials related to identifying mammals having a LTBI. For example, this document provides methods and materials for using ELISpot assays or other interferon-γ release assays to identify mammals (e.g., humans) having a LTBI. As described herein, ELISpot assays that include using anti-CD28 and anti-CD49d antibodies to stimulate the cells can accurately differentiate LTBI from healthy controls. In addition, the ELISpot assays provided herein can identify highly likely LTBIs that are falsely identified as being negative with commercial assays such as QuantiFERON TB Gold In-Tube™ (Cellestis, Australia).

Having the ability to identify humans with a LTBI as described herein can allow clinicians and other medical personnel to identify patients in need of TB treatment in an accurate and efficient manner. In addition, the methods and materials provided herein can help the medical community better target TB prevention strategies to those areas with cases of LTBIs identified as described herein. In some cases, the methods and materials provided herein can be used to assist a qualified clinician and/or healthcare provider in determining whether or not a mammal has a latent tuberculosis infection.

In general, one aspect of this document features a method for determining whether or not a mammal has a latent tuberculosis infection. The method comprises, or consists essentially of, performing an interferon-γ release assay using cells obtained from the mammal, wherein the assay comprises contacting the cells with an anti-CD28 antibody and an anti-CD49d antibody. The mammal can be a human. The mammal can be a human having had a previous TST-positive and IGRA-positive or TST-positive and IGRA-negative test results. The interferon-γ release assay can be an ELISpot assay. Greater than 52 interferon-γ releasing cell spots per $2\times10^5$ cells can indicate that the mammal has a latent tuberculosis infection. In some cases, greater than 30 interferon-γ releasing cell spots per $2\times10^5$ cells can indicate that the mammal has a latent tuberculosis infection. Less than 30 interferon-γ releasing cell spots per $2\times10^5$ cells can indicate that the mammal does not have a latent tuberculosis infection. The cells can be freshly obtained cells. The cells can be cells that were frozen. The cells can be PBMCs. The assay can comprise contacting the cells with $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides.

In another aspect, this document features a method for assisting a qualified clinician and/or healthcare provider in determining whether or not a mammal has a latent tuberculosis infection. The method comprises, or consists essentially of, performing an interferon-γ release assay using cells obtained from the mammal, wherein the assay comprises contacting the cells with an anti-CD28 antibody and an anti-CD49d antibody. The mammal can be a human. The mammal can be a human having had a previous TST-positive and IGRA-positive or TST-positive and IGRA-negative test results. The interferon-γ release assay can be an ELISpot assay. Greater than 52 interferon-γ releasing cell spots per $2\times10^5$ cells can indicate that the mammal has a latent tuberculosis infection. In some cases, greater than 30 interferon-γ releasing cell spots per $2\times10^5$ cells can indicate that the mammal has a latent tuberculosis infection. Less than 30 interferon-γ releasing cell spots per $2\times10^5$ cells can indicate that the mammal does not have a latent tuberculosis infection. The cells can be freshly obtained cells. The cells can be cells that were frozen. The cells can be PBMCs. The assay can comprise contacting the cells with $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides.

In another aspect, this document features a method for identifying a mammal as having a latent tuberculosis infection. The method comprises, or consists essentially of, (a) detecting the presence of greater than a threshold value of interferon-γ releasing cells within a PBMC or whole blood sample obtained from the mammal using an interferon-γ releasing assay, wherein the assay comprises contacting cells of the sample with an anti-CD28 antibody and an anti-CD49d antibody, and (b) classifying the mammal as having the latent tuberculosis infection based at least in part on the presence. The mammal can be a human. The mammal can be a human having had a previous TST-positive and IGRA-positive or TST-positive and IGRA-negative test results. The interferon-γ release assay can be an ELISpot assay. The threshold can be 52 interferon-γ releasing cells per $2\times10^5$ cells. In some cases, the threshold can be 30 interferon-γ releasing cells per $2\times10^5$ cells. The cells can be freshly obtained cells. The cells can be cells that were frozen. The cells can be PBMCs. The assay can comprise contacting the cells with $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides.

In another aspect, this document features a kit comprising, or consisting essentially of, an anti-CD28 antibody and an anti-CD49d antibody for stimulating cells, an anti-interferon-γ capture antibody, and an anti-interferon-γ detection antibody for identifying a number of cells having the ability to release interferon-γ. The kit can comprise an ESAT-6 polypeptide for stimulating cells. The kit can comprise a CFP-10 polypeptide for stimulating cells.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 14 contains results of a TB-ELISPOT (RD1) ROC cut off analysis.

FIG. 15 contains results of a TB-ELISPOT (RD1) TB contact likelihood analysis.

DETAILED DESCRIPTION

Figure 1:
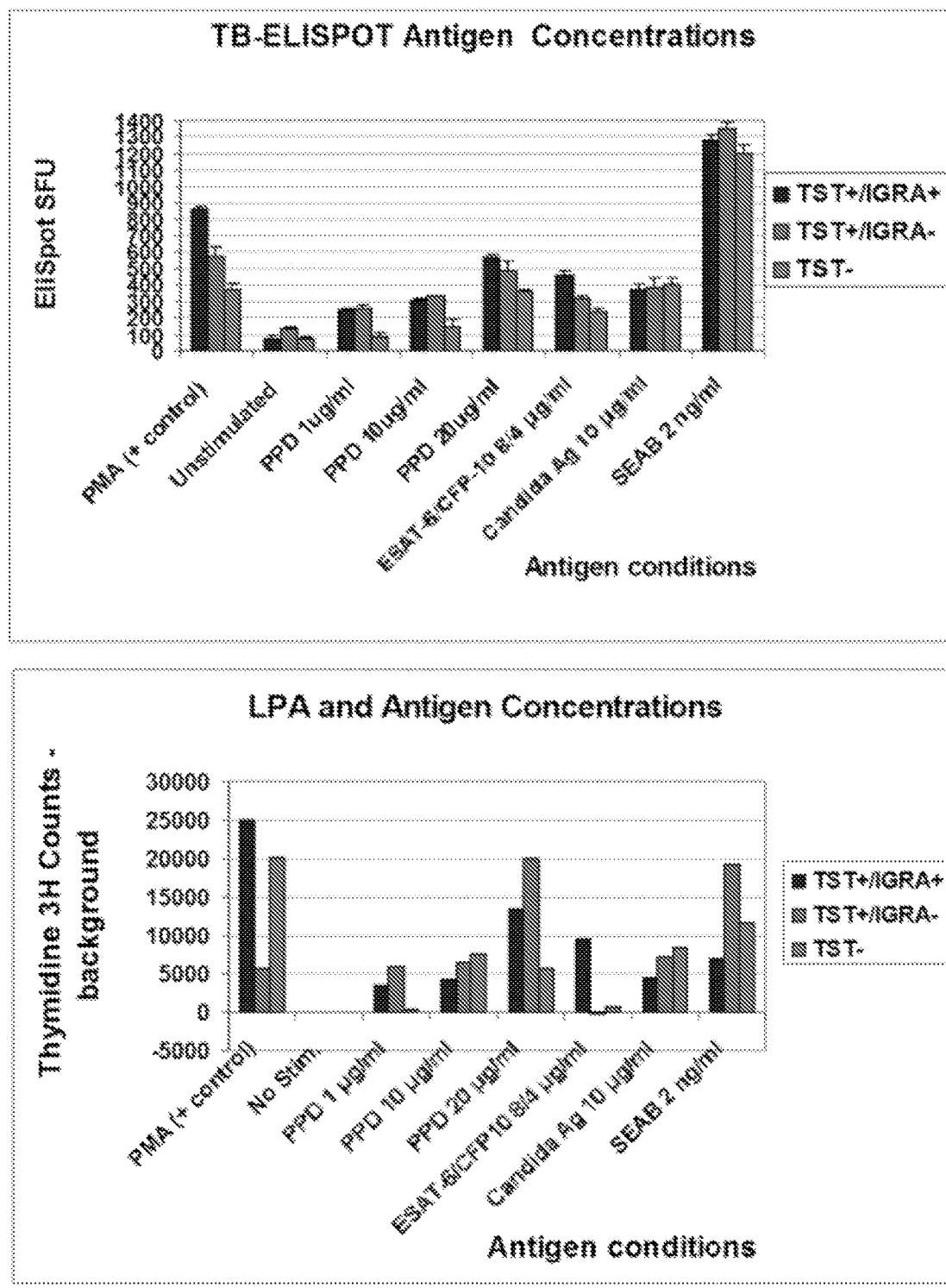
FIG. 1 contains graphs plotting results for a TB-ELISPOT vs. lymphocyte proliferation assay (LPA) validation for the selection of antigen concentrations and assay optimization parameters.
Figure 2:
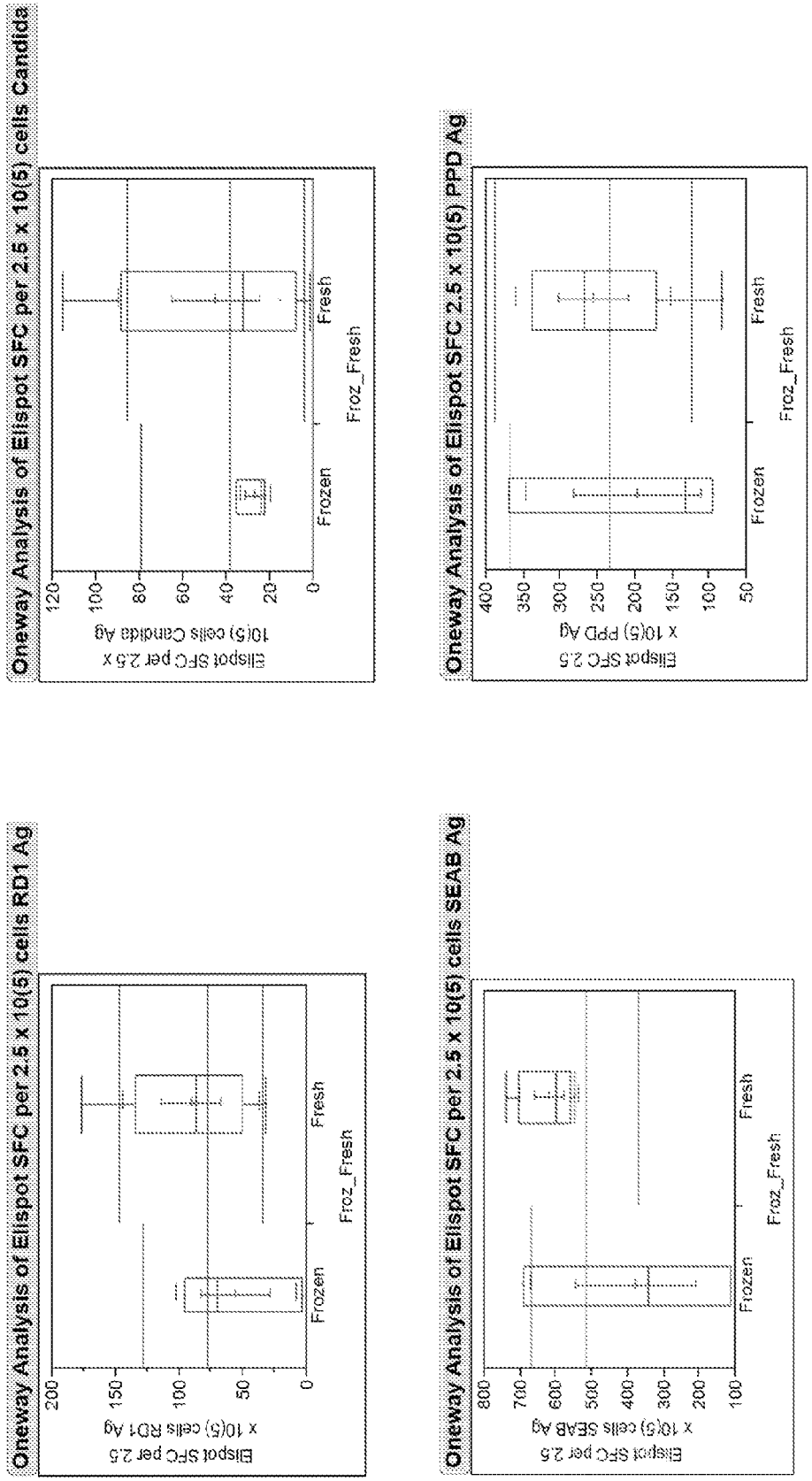
FIG. 2 contains graphs of TB-ELISPOT reproducibility.
Figure 3:
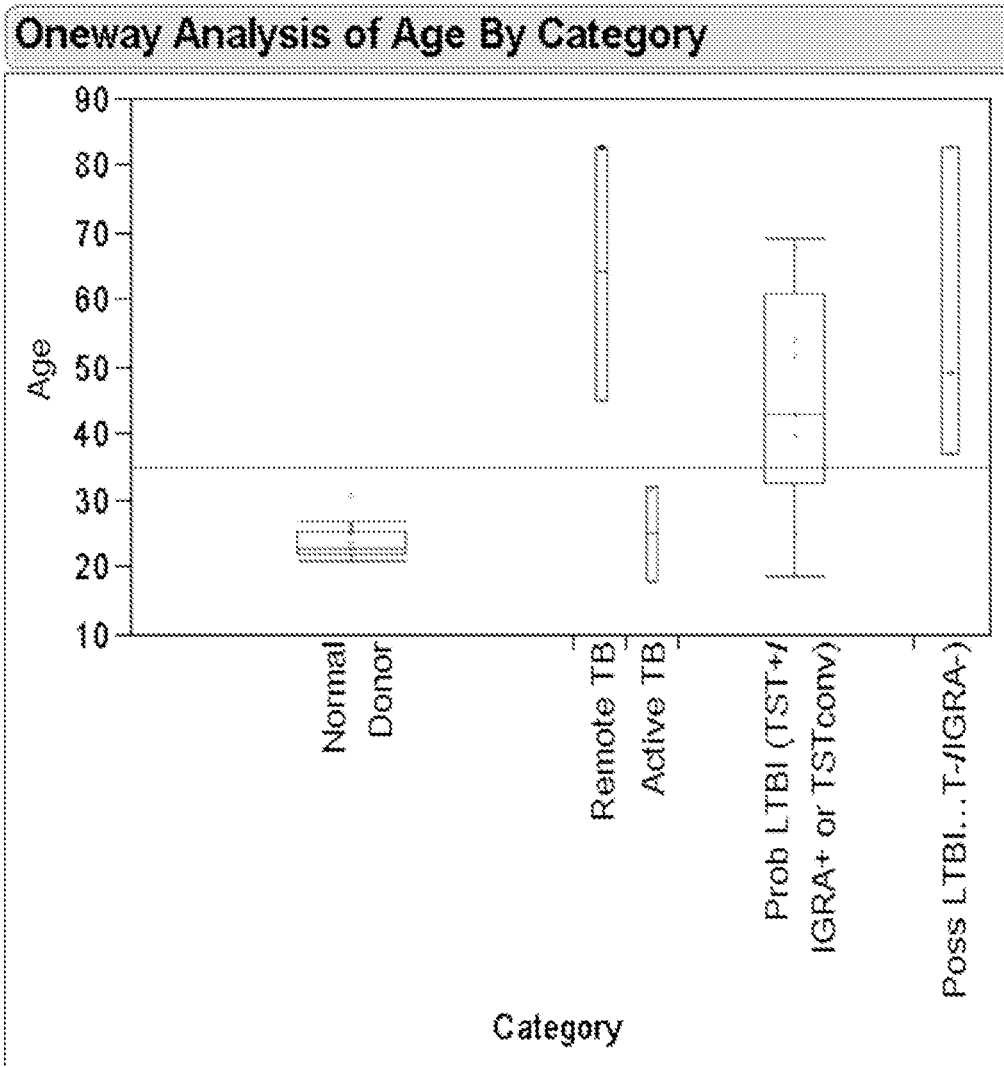
FIG. 3 provides information regarding the study population (N=33).
Figure 4:
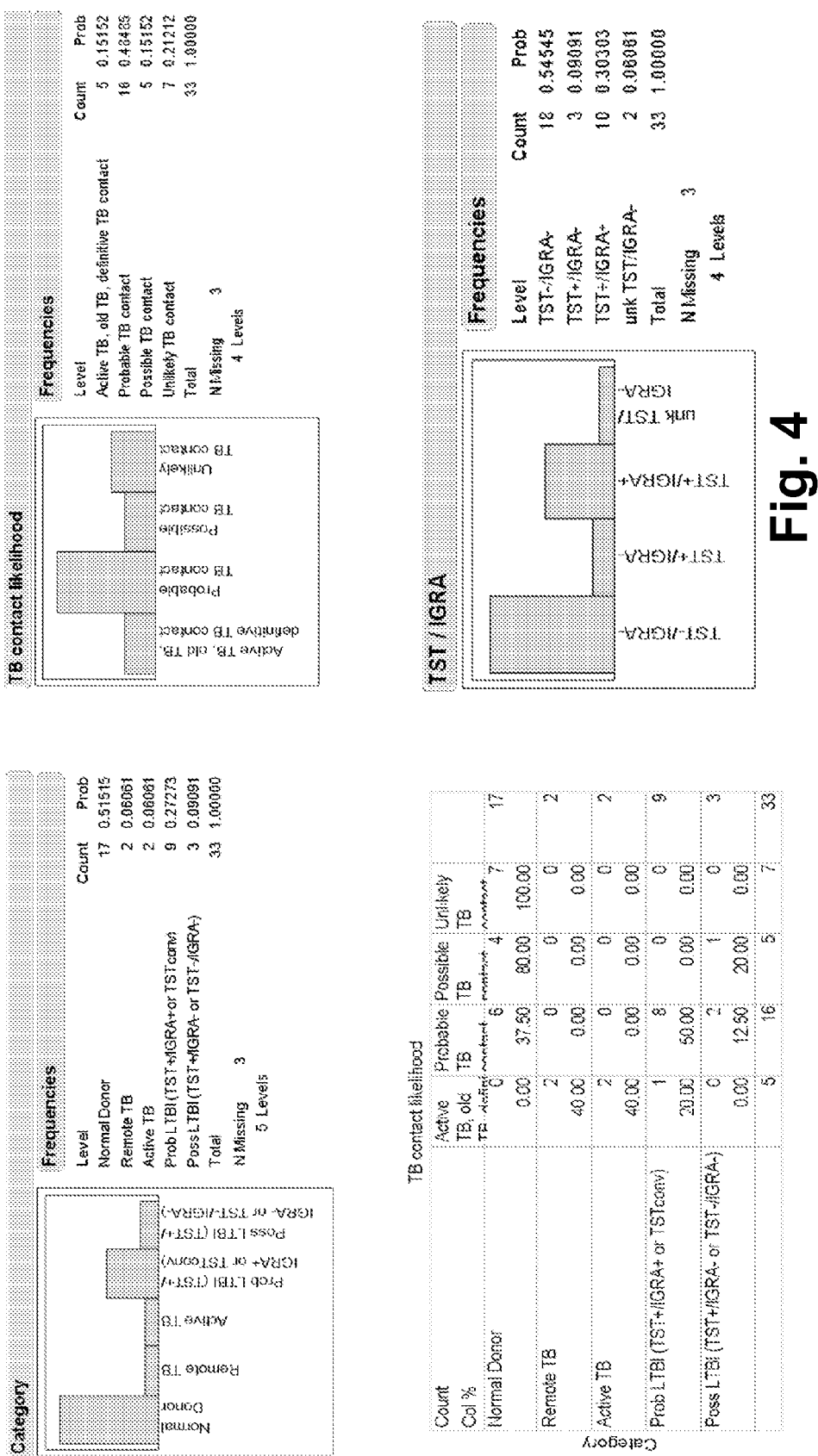
FIG. 4 provides the clinical characteristics (N=33).
Figure 5:
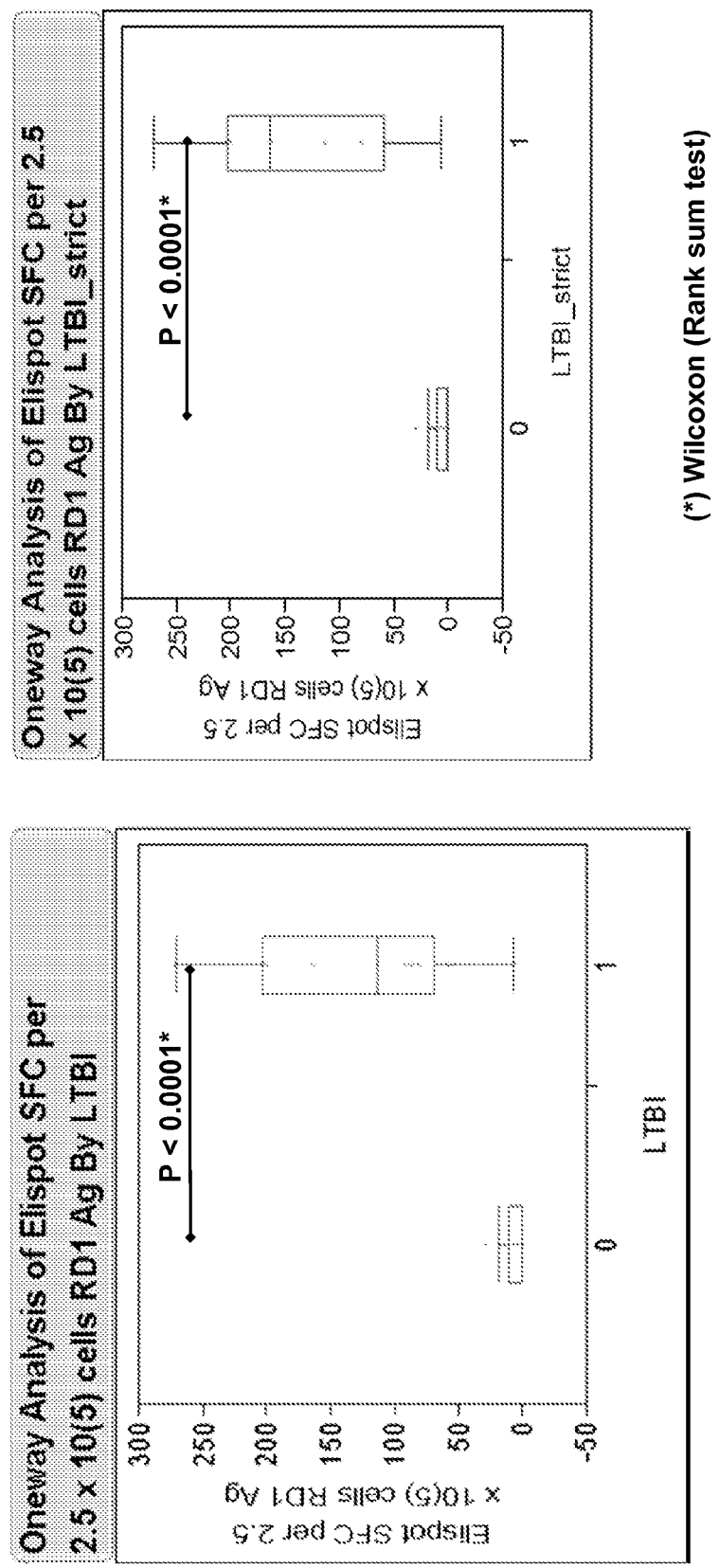
FIG. 5 contains graphs of TB-ELISPOT (RD1) for healthy donors vs. LTBI.
Figure 6:
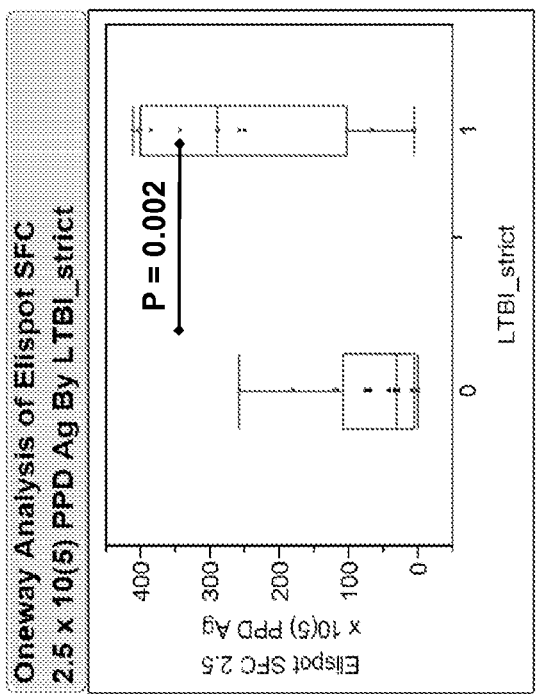
FIG. 6 contains graphs of TB-ELISPOT (PPD) for healthy donors vs. LTBI.
Figure 6:
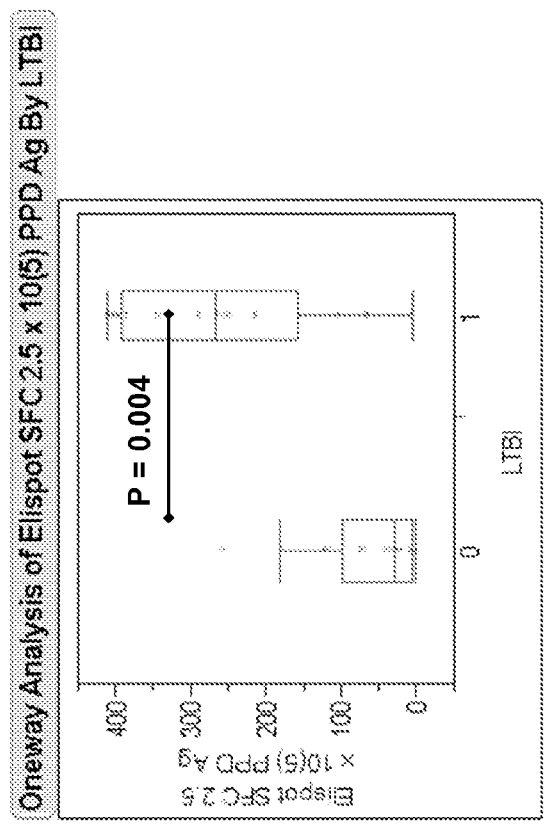
Figure 7:
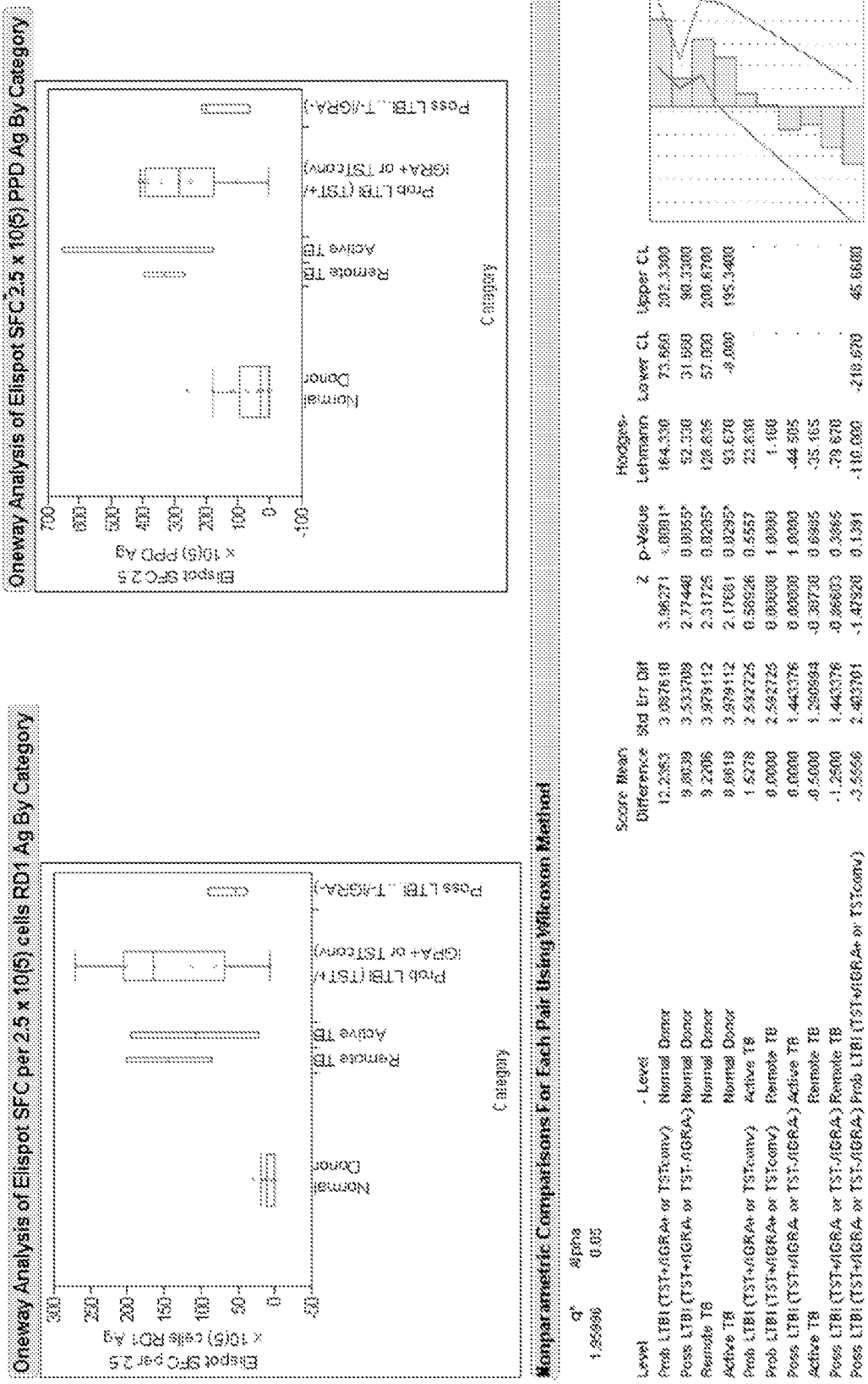
FIG. 7 contains graphs of TB-ELISPOT (RD1 and PPD).
Figure 8:
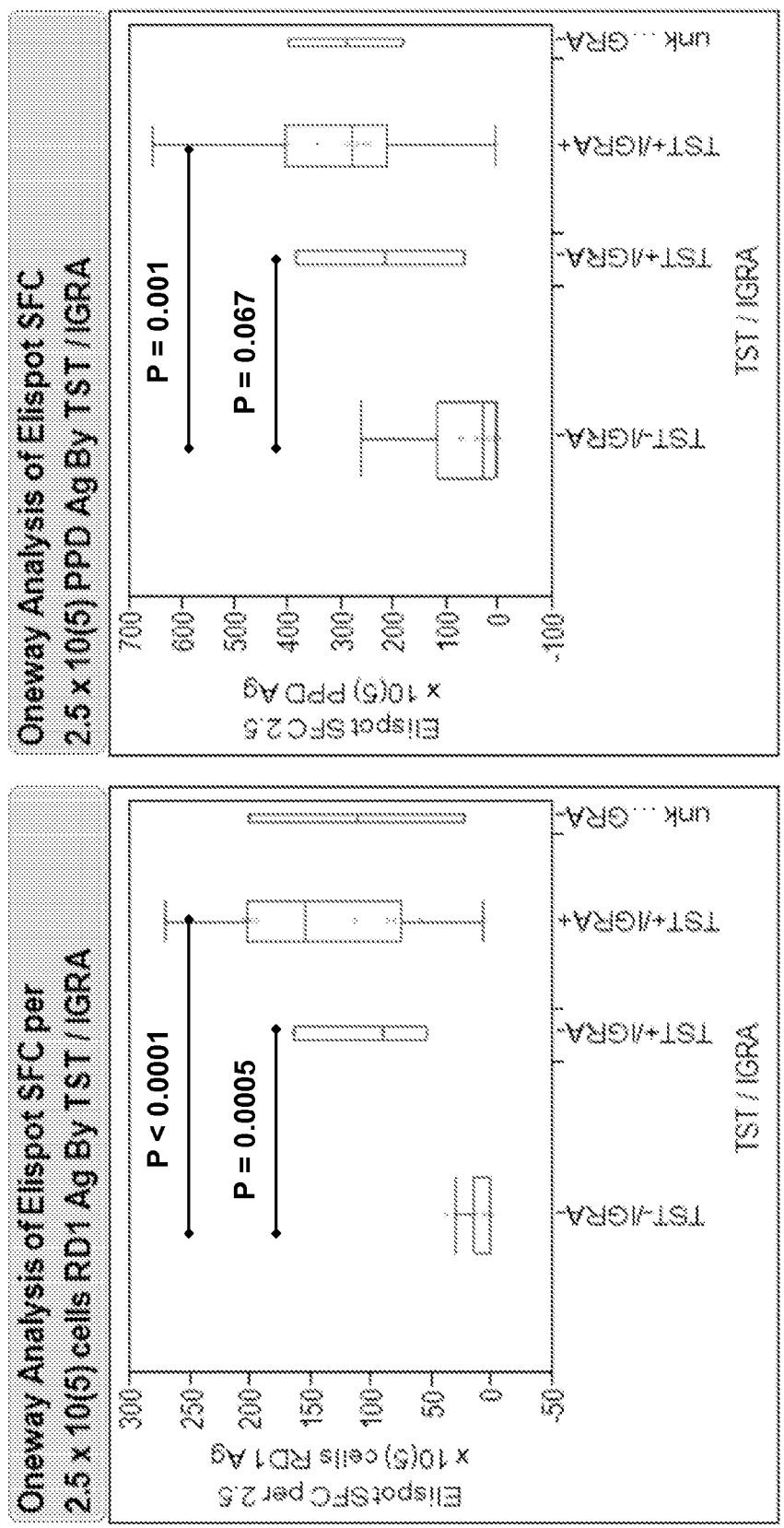
FIG. 8 contains graphs of ELISPOT-TB (RD1 and PPD) by TST/IGRA results.
Figure 9:
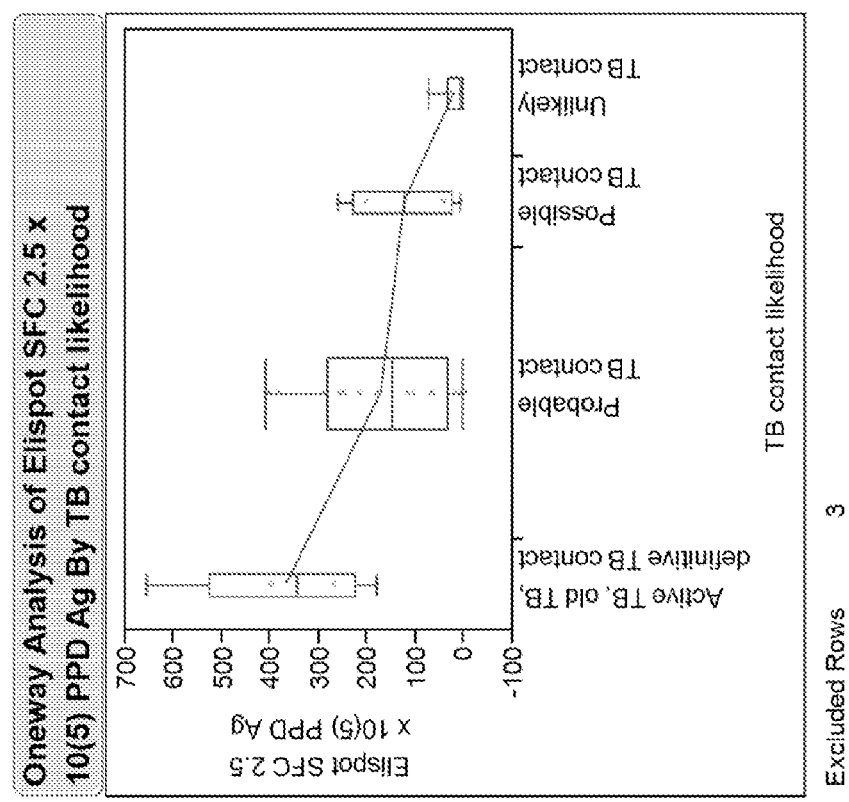
FIG. 9 contains graphs of ELISPOT-TB (RD1 vs. PPD) by TB contact likelihood.
Figure 9:
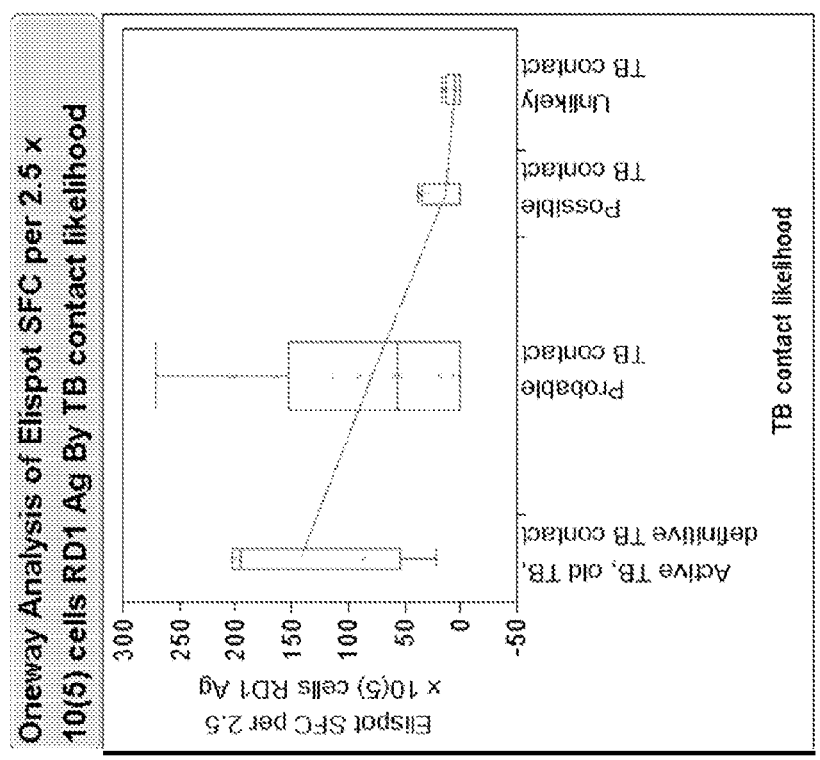
Figure 10:
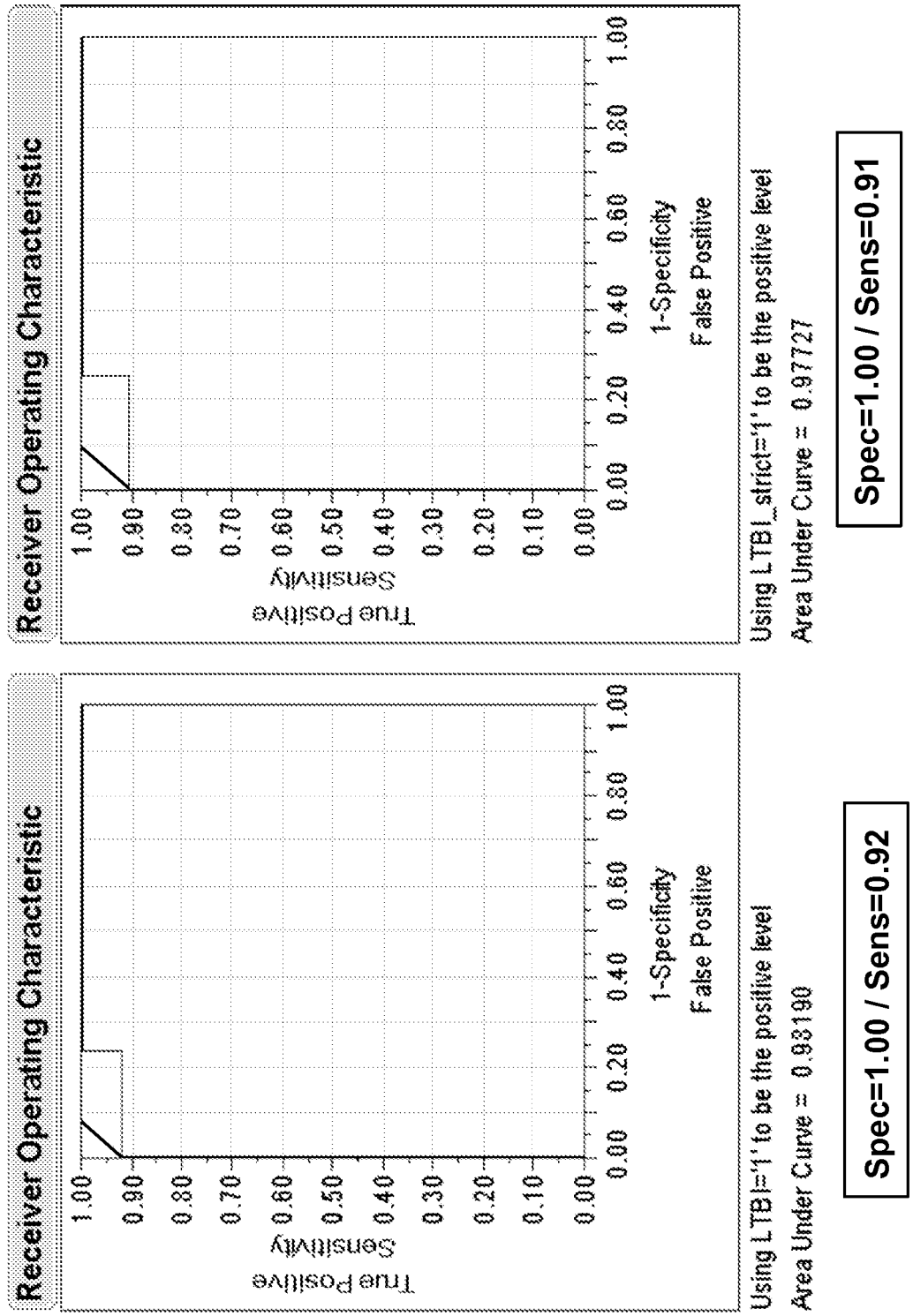
FIG. 10 contains graphs of TB-ELISPOT (RD1): ROC results for LTBI vs. LTBI strict definition.
Figure 11:
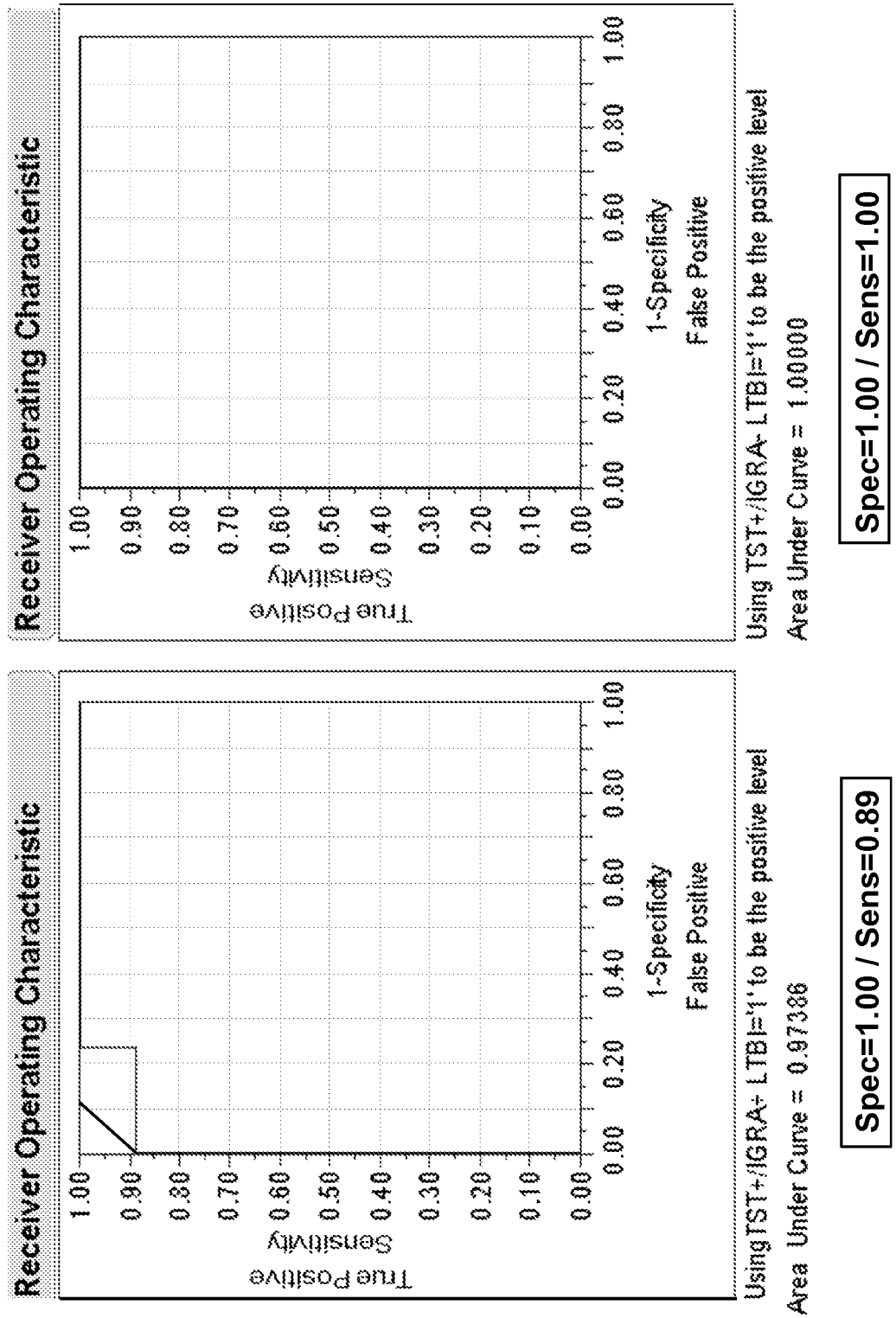
FIG. 11 contains graphs of TB-ELISPOT (RD1): ROC results for TST+/IGRA+vs. TST+/IGRA−.
Figure 12:
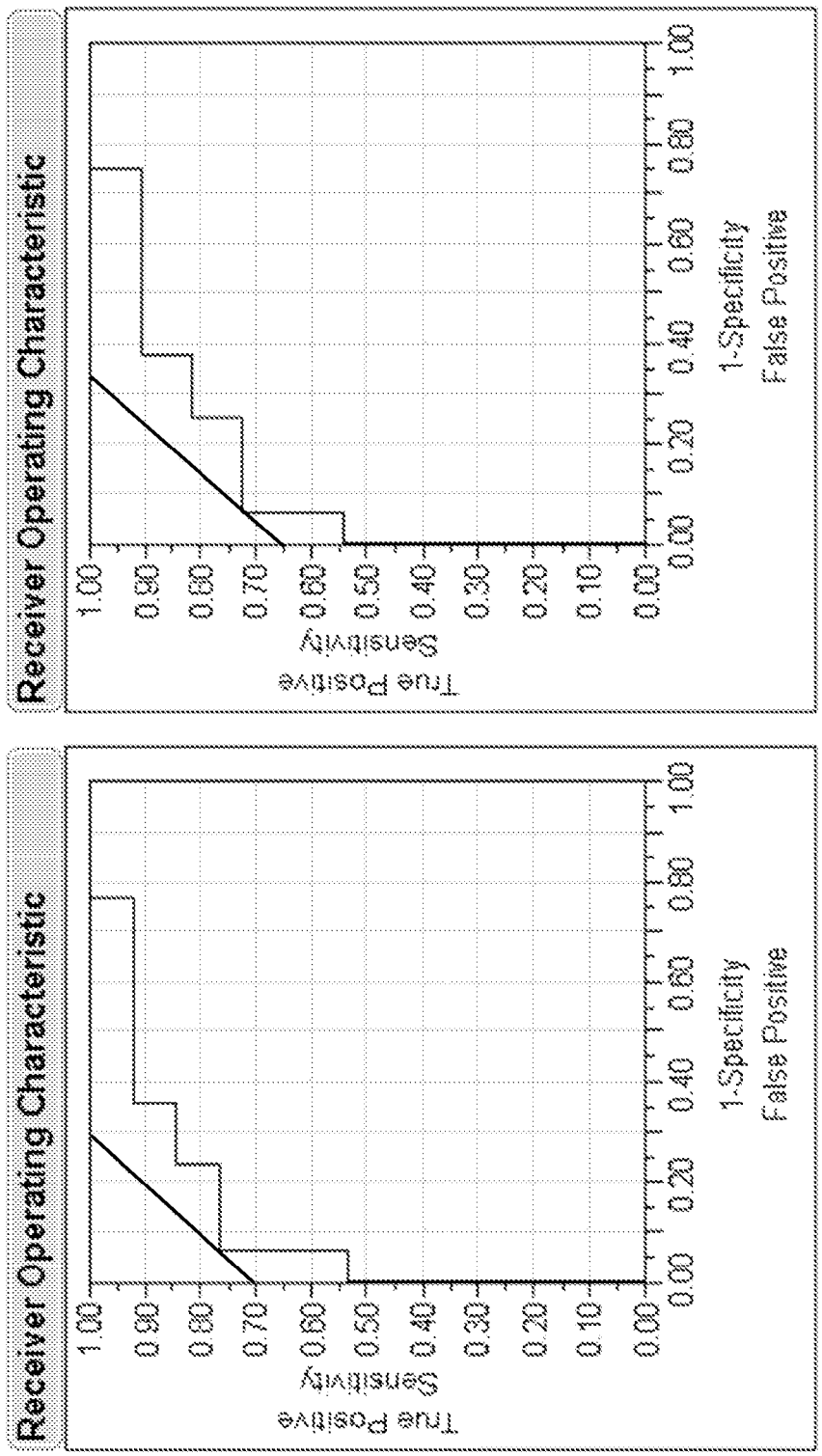
FIG. 12 contains graphs of TB-ELISPOT (RD1): ROC results for TST+/IGRA+vs. TST+/IGRA−.
Figure 13:
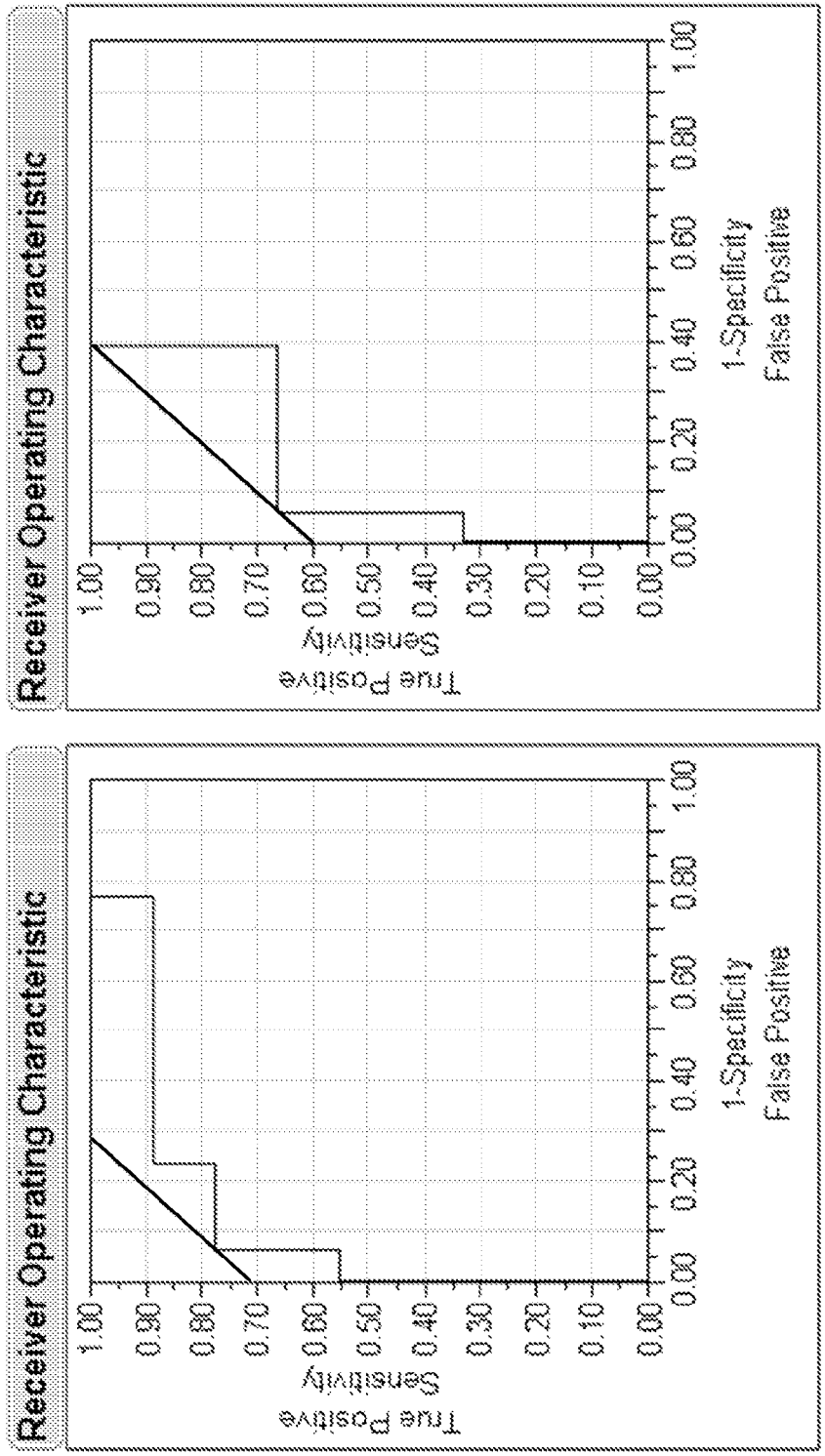
FIG. 13 contains graphs of TB-ELISPOT (PPD): ROC results for TST+/IGRA+vs. TST+/IGRA−.
Figure 16:
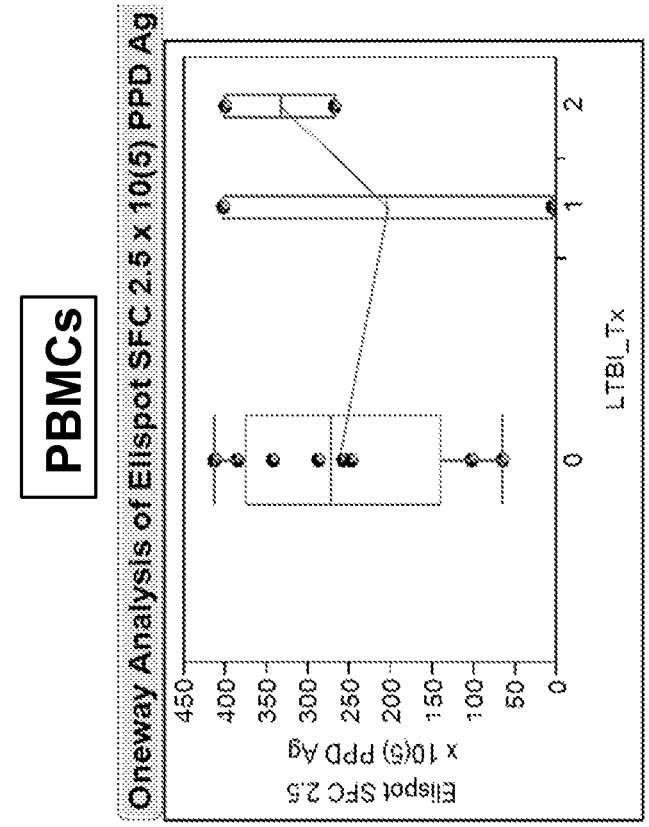
FIG. 16 contains results of an ELISPOT-TB (RD1 vs. PPD) in an analysis of samples from patients undergoing LTBI treatment.
Figure 16:
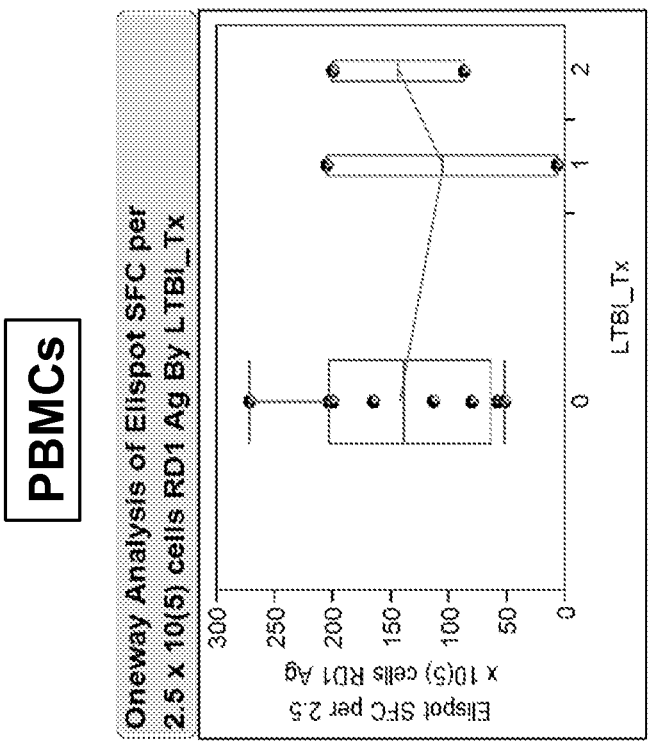
Figure 17:
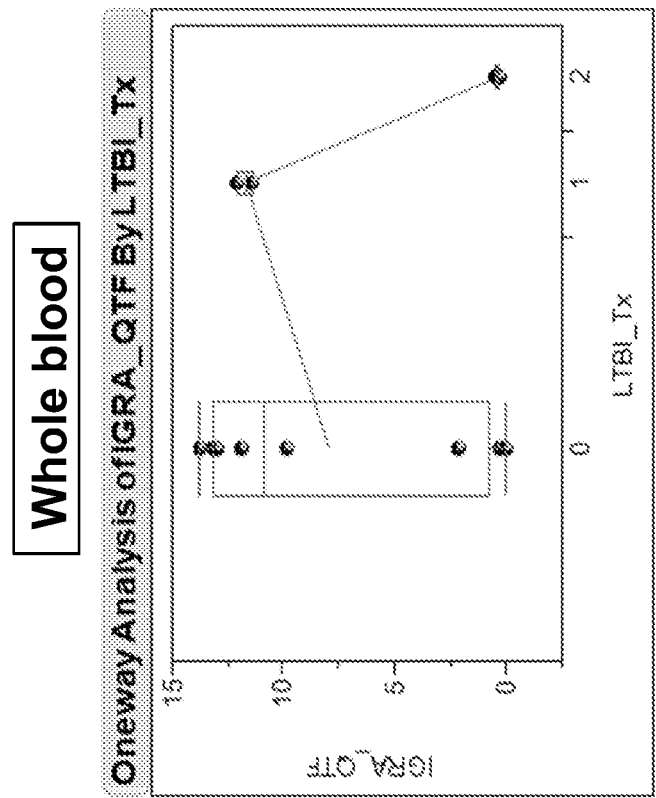
FIG. 17 contains a comparison of ELISPOT-TB (RD1) vs. QuantiFERON GIT™ results in initial LTBI treatment.
Figure 17:
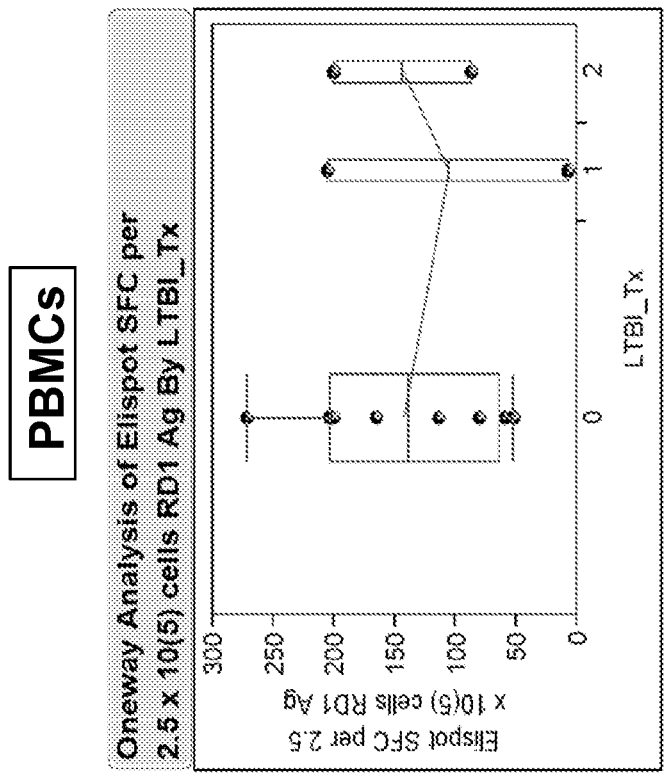

This document provides methods and materials related to identifying mammals having a LTBI. For example, this document provides methods and materials for using ELISpot assays or other interferon-γ release assays to identify mammals (e.g., humans) having a LTBI. An ELISpot assay or interferon-γ release assay provided herein can include incubating cells (e.g., PBMCs or cells from a whole blood sample) with a stimulation preparation. The cells can be freshly obtained cells or cells that have been stored or frozen. The stimulation preparation can include a mixture of ESAT-6 and CFP-10 polypeptides. For example, a stimulation preparation can include a mixture of $ESAT-6_{1-20}$, $ESAT-6_{31-50}$, $ESAT-6_{42-65}$, $ESAT-6_{61-80}$, $CFP-10_{51-70}$, and $CFP-10_{71-90}$ polypeptides. In some cases, a stimulation preparation can include a combination of an anti-CD28 antibody and an anti-CD49d antibody. Any appropriate length of time can be used for the incubation period. For example, the cells can be incubated as 37° C. for between 25 and 90 hours (e.g., between 25 and 86 hours, between 25 and 60 hours, or between 35 and 45 hours).

Once the cells are treated with the stimulation preparation, they can be assessed for the ability to release interferon-γ using the detection techniques of, for example, an ELIspot assay. For example, the cells exposed to a stimulation preparation (e.g., about $2 \times 10^5$ cells) can be added to wells coated with anti-interferon-γ capture antibodies, and enzymes and anti-interferon-γ detection antibodies can be used identify the number of cells having the ability to release interferon-γ. In some cases, a positive ELISpot result for a TB infection or disease can be recorded when the mean ELISpot count from three EliSpot plates with a mixture of ESAT-6 and CFP-10 polypeptides minus the mean ELISpot count from three ELISpot plates with unstimulated PBMC samples is greater than or equal to about 45 (e.g., about 46, 47, 48, 49, 50, 51, 52, 54, or 56) per $2\times10^5$ cells. In some cases, a positive ELISpot result for a TB infection can be recorded when the mean ELISpot count from three EliSpot plates with a mixture of ESAT-6 and CFP-10 polypeptides minus the mean ELISpot count from three ELISpot plates with unstimulated PBMC samples is greater than or equal to about 28 (e.g., about 29, 30, 31, 32, 33, 34, 35, 36, or 38) per $2\times10^5$ cells.

This document also provides kits for identifying mammals having a LTBI. For example, reagents of a stimulation preparation and reagents for assessing the release interferon-γ can be combined as an article of manufacture such as a kit. In one embodiment, a kit can contain an anti-CD28 antibody and an anti-CD49d antibody for stimulating cells and an anti-interferon-γ capture antibody and an anti-interferon-γ detection antibody to identify the number of cells having the ability to release interferon-γ. In another embodiment, a kit can contain ESAT-6 polypeptides and CFP-10 polypeptides for stimulating cells and an anti-interferon-γ capture antibody and an anti-interferon-γ detection antibody to identify the number of cells having the ability to release interferon-γ. In another embodiment, a kit can contain an anti-CD28 antibody, an anti-CD49d antibody, ESAT-6 polypeptides, and CFP-10 polypeptides for stimulating cells and an anti-interferon-γ capture antibody and an anti-interferon-γ detection antibody to identify the number of cells having the ability to release interferon-γ.

In some cases, a kit can contain buffers, positive control samples, or combinations thereof. The reagents within a kit can be housed together in various combinations or can be packaged in separate vials or containers. The kits provided herein also can include labels or packaging inserts setting out instructions for preparation and use. For example, a kit can contain a packaging insert describing that a positive ELISpot result for a TB infection or to support a diagnosis of LTBI can be recorded when the mean ELISpot count from three EliSpot plates with a mixture of ESAT-6 and CFP-10 polypeptides minus the mean ELISpot count from three ELISpot plates with unstimulated PBMC samples is greater than or equal to about 28 (e.g., about 29, 30, 31, 32, 33, 34, 35, 36, or 38) or greater than or equal to about 45 (e.g., about 46, 47, 48, 49, 50, 51, 52, 53, 54, or 56) per $2\times10^5$ cells.

The invention will be further described in the following examples, which do not limit the scope of the invention described in the claims.

EXAMPLES

Example 1—An Enhanced ELISpot Interferon-Gamma Release Assay for Detecting Latent Tuberculosis Infection This following ELISpot assay protocol was developed to detect LTBIs. The following eight steps are performed on day 1 of the assay.

1. Prepare cell culture media: Use a conical tube; add 50 mL RPMI 1640 (with 2 mM L-glutamine) supplemented with 10% human AB serum and 0.5 mL of Pen-Strep mixture (Gibco #15140-122) to final concentration of penicillin 100 IU/mL and streptomycin (100 μg/mL) in culture medium.

2. Within 2 hours of blood collection in heparinized tubes (total 20 cc), harvest peripheral blood monocytes (PBMC) using a density gradient centrifugation of whole blood (Ficoll-Plaque™ technique), wash cells two times with PBS and add cell culture media in a polypropylene sterile tube for a final concentration $2.5\times10^6$ PBMCs/mL.

3. Perform stimulation procedures with PBMC's using concentration of (a) *Staphylococcus* Enterotoxin A and B (SEAB) or other super antigen or mitogen (e.g., phytohemagglutinin (PHA)), (b) tuberculin PPD™ (Staten Serum Institute, Denmark), (c) RD1-peptide mix (ESAT-6 and CFP-10 peptides mix), or (d) *Candida* protein mix. An unstimulated sample is used as a control. Four ESAT-6 polypeptides and two CFP-10 polypeptides are included in the RD1-peptide mix. The ESAT-6 polypeptides are ESAT-$6_{1-20}$ (MTEQQWNFAGIEAAASAIQG; SEQ ID NO:1), ESAT-$6_{31-50}$ (EGKQSLTKLAAAWGGSGSEA; SEQ ID NO:2), ESAT-$6_{42-65}$ (AWGGSGSEAYQGVQQKW-DATATEL; SEQ ID NO:3), and ESAT-$6_{61-80}$ (TATELN-NALQNLARTISEAG SEQ ID NO:4). The CFP-10 polypeptides are CFP-$10_{51-70}$ (AQAAVVRFQEAANKQKQELD; SEQ ID NO:5) and CFP-$10_{71-90}$ (EISTNIRQAGVQYSRADEEQ; SEQ ID NO:6).

4. Keep 2.5 mL of blood sample for whole blood experiments using the following antigen stimulation conditions and controls.

5. Stimulation procedure (under the hood):
   a. Tube 1 (SEAB to final concentration at 2 ng/mL w/v—same final concentration as per PMBC's stimulation conditions):
      i. Dilute 24 μL of freshly thawed SEAB stock (0.5 ng/μL) and in 476 μL of culture media.
      ii. Then add 3 mL of diluted fresh SEAB to 3 mL of whole blood from Sodium heparin sample to tube 1 (total of 3 mL).
   b. Tube 2 (PPD final concentration of 20 μg/mL—same final concentration as per PMBCs stimulation conditions):
      i. Tube 2: "PPD": Add 60 μL of PPD in 1.44 mL of culture media.
      ii. Then add 1.5 mL of diluted PPD and 1.5 mL of whole blood from Sodium heparin sample to tube 2 ("PPD at 20 μg/mL") (3 mL total).
   c. Tube 3 (CFP-10+ESAT-6 peptide mix same final concentrations per PMBC's stimulation conditions):
      i. Tube 3: "CFP-10 (add at 4 μg/mL)/ESAT-6 mix (add at 2 μg/mL)": all stock is 1 μg/μL. Add 12 μL of CFP10 and add 6 μL of ESAT-6 with 1.49 mL of culture media.
      ii. Add 1.5 mL of diluted fresh CFP-10/ESAT-6 in culture media at 1.5 mL of whole blood from sodium heparin sample to tube: (3 mL total).
   d. Tube 4 (*Candida* activated same final concentration as per PMBC's stimulation conditions):
      i. Dilute 3 μL of *Candida* stock solution (10 μg/μL) in 1.5 mL of culture media ("*Candida* to 10 μg/mL in culture media").
      ii. Then add 1.5 mL of diluted *Candida* and 1.5 mL of whole blood from Sodium heparin sample to tube (3 mL total).

6. Tube 5 ("unstimulated blood"):
   a. Use 1.5 mL of whole blood from Sodium heparin sample for tube 5, then add 1.5 mL of culture medium to dilute 1:1.

7. Add 5 μL of anti-CD28/anti-CD49d reagent (Becton Dickinson FastImmune™ CD28/CD49d Costimulatory Reagent; BD Biosciences cat#347690) to activated tubes (Tubes 2, 3, 4, and 5) and vortex gently.

8. Incubate all tubes in a $CO_2$ incubator at 37° C. for about 40 hours. ELIspot plates (Millipore, Billerica, Mass.) are coated with 10 µg/mL IFN-γ capture antibody (MabTech USA, Mariemont, Ohio), and are incubated overnight. The plates are then washed with PBS and are blocked with medium for 2 hours. $2.5 \times 10^5$ cells per well plus stimuli are added in 200 µL media and are incubated at 37° C. for 40 hours. Each sample is evaluated in triplicate.

After washing with PBS containing 0.05% tween-20, 2 µg/mL of biotinylated secondary antibody for IFN-γ (MabTech USA, Mariemont, Ohio) is added, and the plates are incubated for 2 hours at 37° C. followed by another wash. Next, 1 µL of Streptavidin-horseradish peroxidase (BD Pharmingen, San Diego, Calif.) per mL of 10% FBS in phosphate-buffered saline (PBS) is added, and the plates are incubated for 1 hour at room temperature. For the final wash, plates are first washed with PBS containing 0.05% Tween-20, followed by washing with PBS. Plates are developed by adding 20 µL of AEC (3-amino-9-ethyl-carbazole) chromogen per mL of AEC substrate (Sigma-Aldrich). The reaction is stopped with water. After drying overnight, the plates are read on an AID EliSpot reader (SanDiego, Calif.), which provides quantitative spot information based on the number of stimulated cells that secrete IFN-γ.

A positive ELISpot result for a TB infection or in support of LTBI diagnosis is recorded when the mean ELISpot count from 3 EliSpot plates with RD1-peptides minus the mean ELISpot count from 3 ELISpot plates with unstimulated PBMC samples is greater than or equal to 52.33 per $2 \times 10^5$ cells. In some cases, a positive ELISpot result for a TB infection or in support of LTBI diagnosis is recorded when the mean ELISpot count from 3 EliSpot plates with RD1-peptides minus the mean ELISpot count from 3 ELISpot plates with unstimulated PBMC samples is greater than or equal to 30.34 per $2 \times 10^5$ cells.

Example 2—Detecting Latent Tuberculosis Infection with an Enhanced ELISpot Interferon-Gamma Release Assay The following was performed to test the diagnostic performance of the ELISpot interferon-γ release assay set forth in Example 1 (referred to as TB-ELISPOT) in subjects with low to high probability of LTBI. Briefly, PBMCs were incubated for 40 hours with specific TB antigens and controls, using co-stimulatory antibodies. Spot counts in subjects with low probability of LTBI (TST-negative and concurrent commercial IGRA-negative results) and highly likely LTBI cases were compared. The area under the curve(AUC) of ROC was analyzed, and the optimal cut off values that differentiate these populations were determined and applied to the selected test cases.

32 subjects were enrolled, including 17 normal subjects with TST-neg/IGRA-neg results, and highly likely LTBI cases (nine TST-pos/IGRA-pos, one TST conversion (TST-pos/IGRA-neg), and one old-healed TB case). TB-ELISPOT AUC of ROC for LTBI was 0.98 (sensitivity=91%; specificity=100%) at the optimal cut off of 52 spot counts. TB-ELISPOT was positive in an old-healed TB case treated with thoracoplasty (IGRA-neg), and 3 out of 3 patients with possible TB exposure and TST-pos/IGRA-neg results. One case of active TB on immunosuppressors and one chronic lymphocytic leukemia (CLL) patient with TST-pos/IGRA-pos results had TB-ELISPOT spot counts below the optimal cut off value. Kappa statistics for LTBI with either TST-pos/IGRA-pos or TST-pos/IGRA-neg results was 0.93 (95% CI 0.79, 1.06; P<0.0001).

The diagnostic performance of TB-ELISPOT was compared with simultaneous commercial IGRA in a patient population with low, intermediate, and high risk of LTBI, and with either discordant or concordant previous TST/IGRA results (FIG. 1). TB-ELISPOT accurately differentiated normal donors from highly suspected LTBI cases, including the ones with TST-pos/IGRA-neg results. TB-ELISPOT exhibited a higher rate of detection of antigen-specific T-cell activation to RD1 antigens compared with commercial IGRA, allowing a more accurate detection of LTBI in patients with discordant TST-pos/IGRA-neg results. Additional results are provided in FIGS. 2-17. The results for FIGS. 3-17 involved the analysis of 33 subjects.

These results demonstrate that an enhanced ELISpot technique for TB can be performed with a high diagnostic yield. TB-ELISPOT detected some false negative IGRA results. These results also demonstrate that false negative TB-ELISPOT results can occur with immunosuppression. In addition, these results demonstrate that TB-ELISPOT with RD1 and PPD can accurately differentiate LTBI versus healthy controls. TB-ELISPOT (with RD1>PPD) appeared to detect LTBI in TST-pos/IGRA-neg cases. TB-ELISPOT (RD1) appeared to have the highest diagnostic performance for LTBI with either TST-pos/IGRA-pos or TST-pos/IGRA-neg cases.

Example 3—Detecting Latent Tuberculosis Infection with an Enhanced ELISpot Interferon-Gamma Release Assay The study set forth in Example 2 was expanded to include an additional 40 subjects for a total of 72. In addition, of the original 17 normal subjects with TST-neg/IGRA-neg results, six were classified as being probable for a prior TB exposure, and four were classified as being possible for a prior TB exposure. Thus, the data was reanalyzed and included only healthy subjects with unlikely prior TB exposures (10 subjects) as negative controls to more accurately study the diagnostic performance of the assay.

Briefly, PBMCs were incubated for 40 hours with specific TB antigens and controls, using co-stimulatory antibodies. Spot counts in subjects with low probability of LTBI (TST-negative and concurrent commercial IGRA-negative results) and highly likely LTBI cases were compared. The area under the curve (AUC) of ROC was analyzed, and the optimal cut off values that differentiate these populations were determined and applied to the selected test cases.

As explained above, 72 subjects were enrolled, including 10 normal subjects with TST-neg/IGRA-neg results (and unlikely to have had prior TB contact), and highly likely LTBI cases (ten TST-pos/IGRA-pos, three TST conversion (TST-pos/IGRA-neg), and one old-healed TB case). TB-ELISPOT AUC of ROC for a strict definition of LTBI was 0.97 (sensitivity=93%; specificity=100%) at the optimal cut off of 30 spot counts. TB-ELISPOT ELISPOT was positive in an old-healed TB case treated with thoracoplasty (IGRA-neg), two healthcare workers with prior close contact with TB patients, and three patients with recent TST conversion and risk factors for LTBI and TST-pos/IGRA-neg results. One case of active TB on immunosuppressors and one patient with prior history of TST-pos and suboptimal compliance with LTBI therapy 10 years prior to having IGRA-pos test results exhibited TB-ELISPOT spot counts below the optimal cut off value of 30.34. Cohen's kappa coefficient for LTBI with TST-pos/IGRA-pos results was 0.86 (95% CI 0.64, 1.05; P<0.0001). Cohen's kappa coefficient for LTBI with TST-pos/IGRA-neg results was 0.59 (95% CI 0.26, 0.91; P=0.005).

Figure 18:
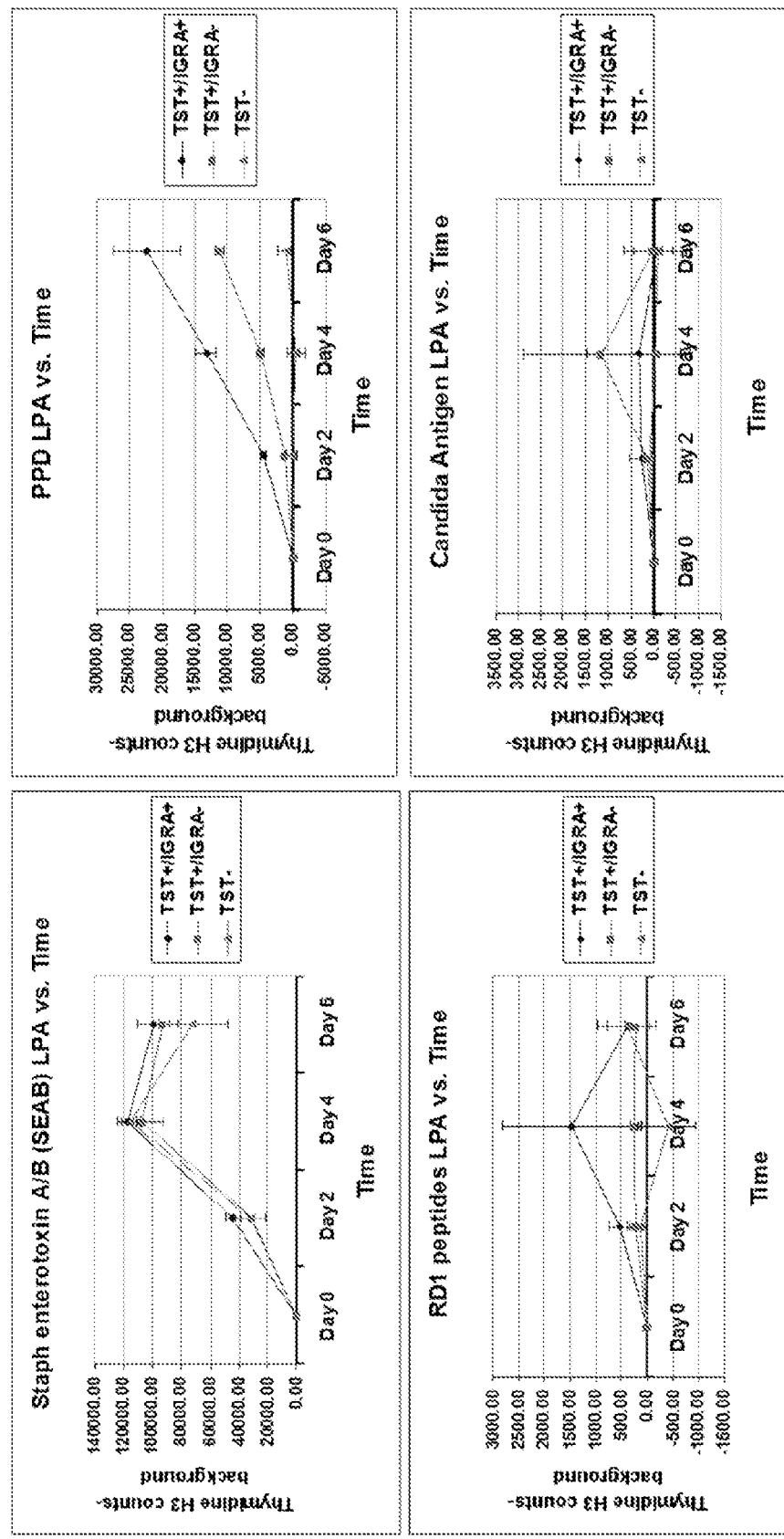
FIG. 18 contains graphs plotting results for a TB-ELISPOT vs. lymphocyte proliferation assay (LPA) validation for the selection of antigen concentrations and assay optimization parameters.
Figure 19:
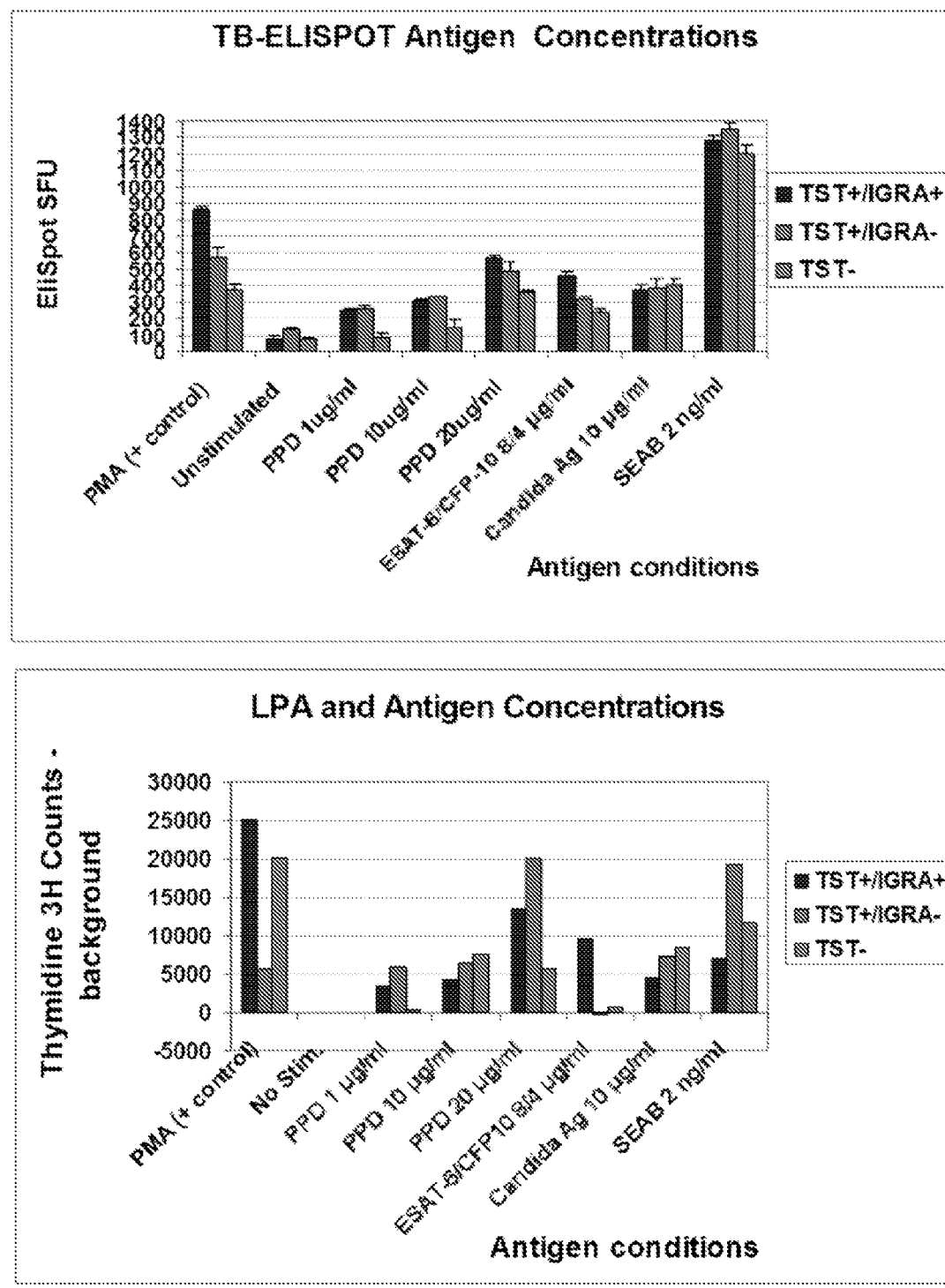
FIG. 19 contains graphs of TB-ELISPOT and LPA validation (antigen concentrations and assay optimization).
Figure 20:
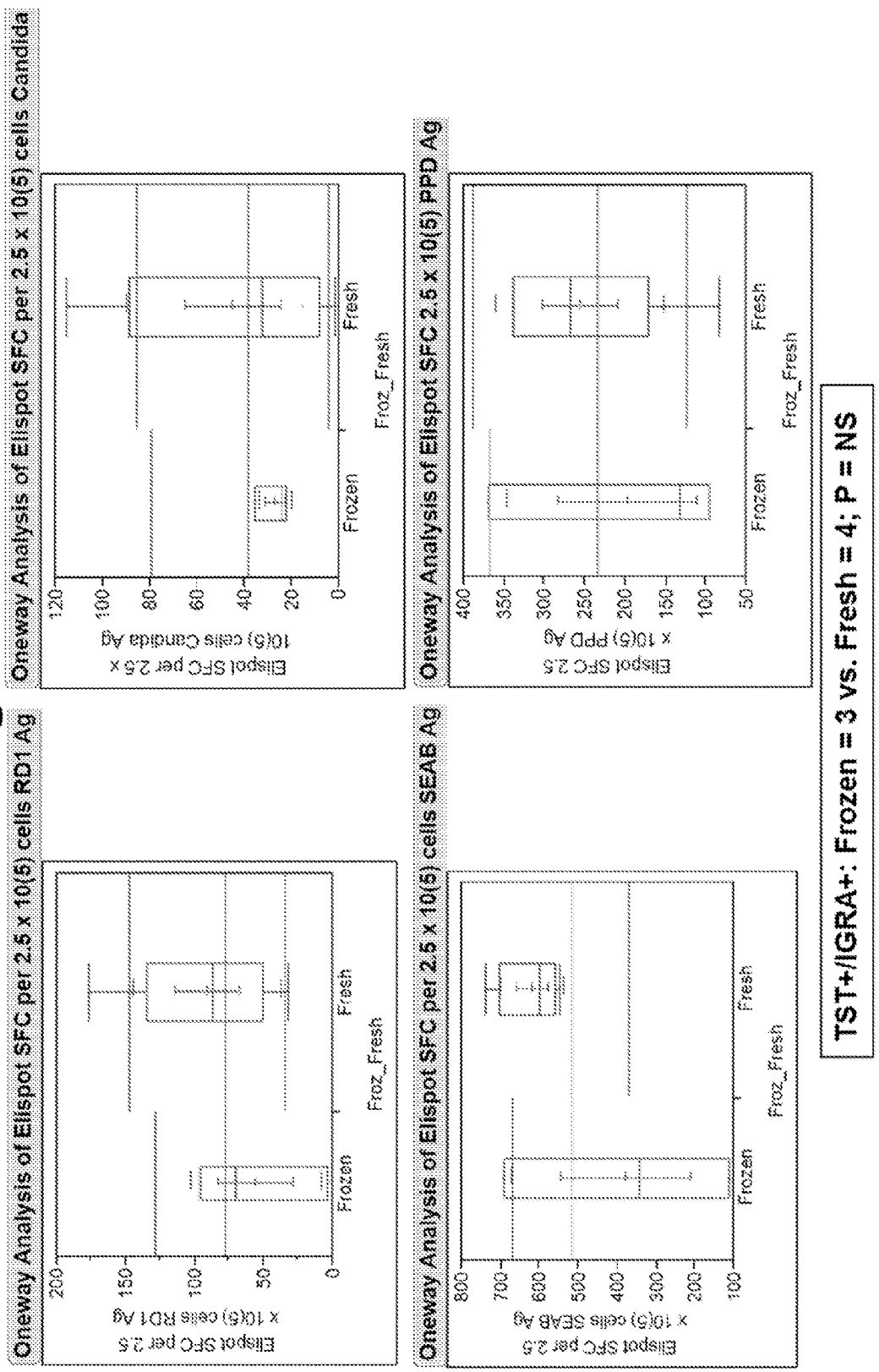
FIG. 20 contains graphs of TB-ELISPOT reproducibility.
Figure 21:
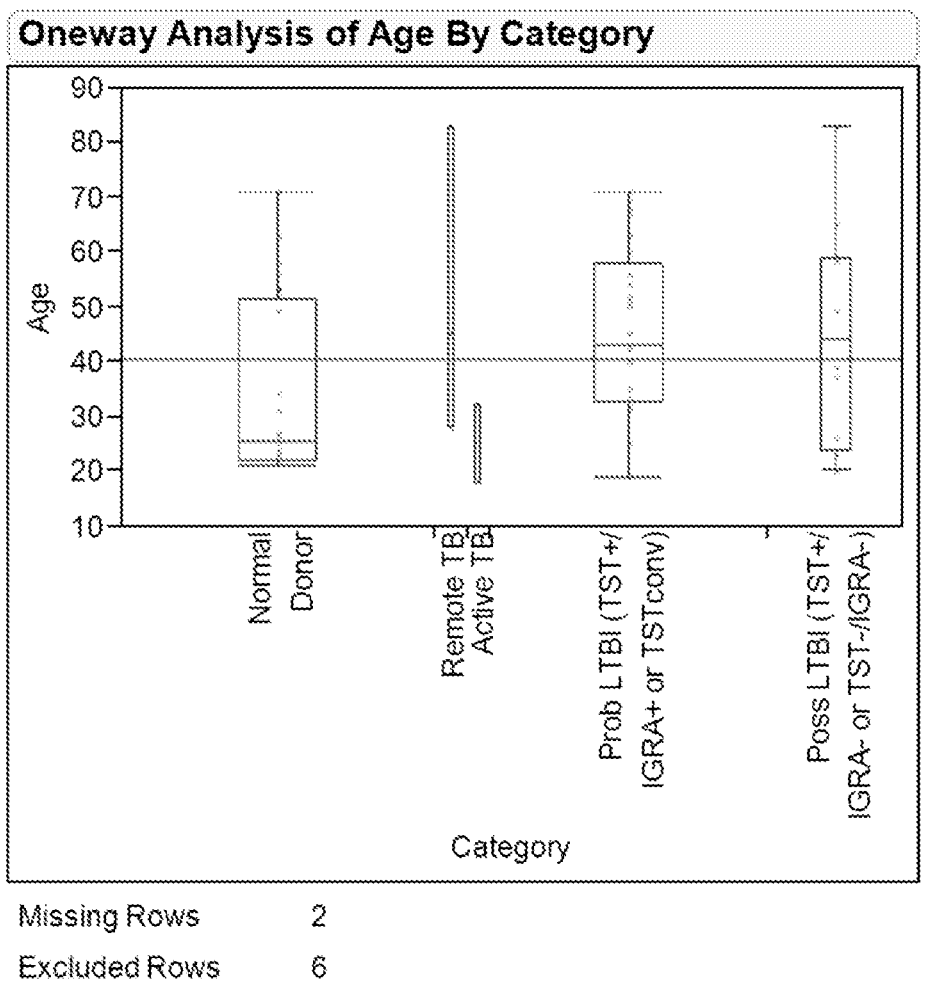
FIGS. 21 and 22 provide information regarding the study population (N=72).
Figure 22:
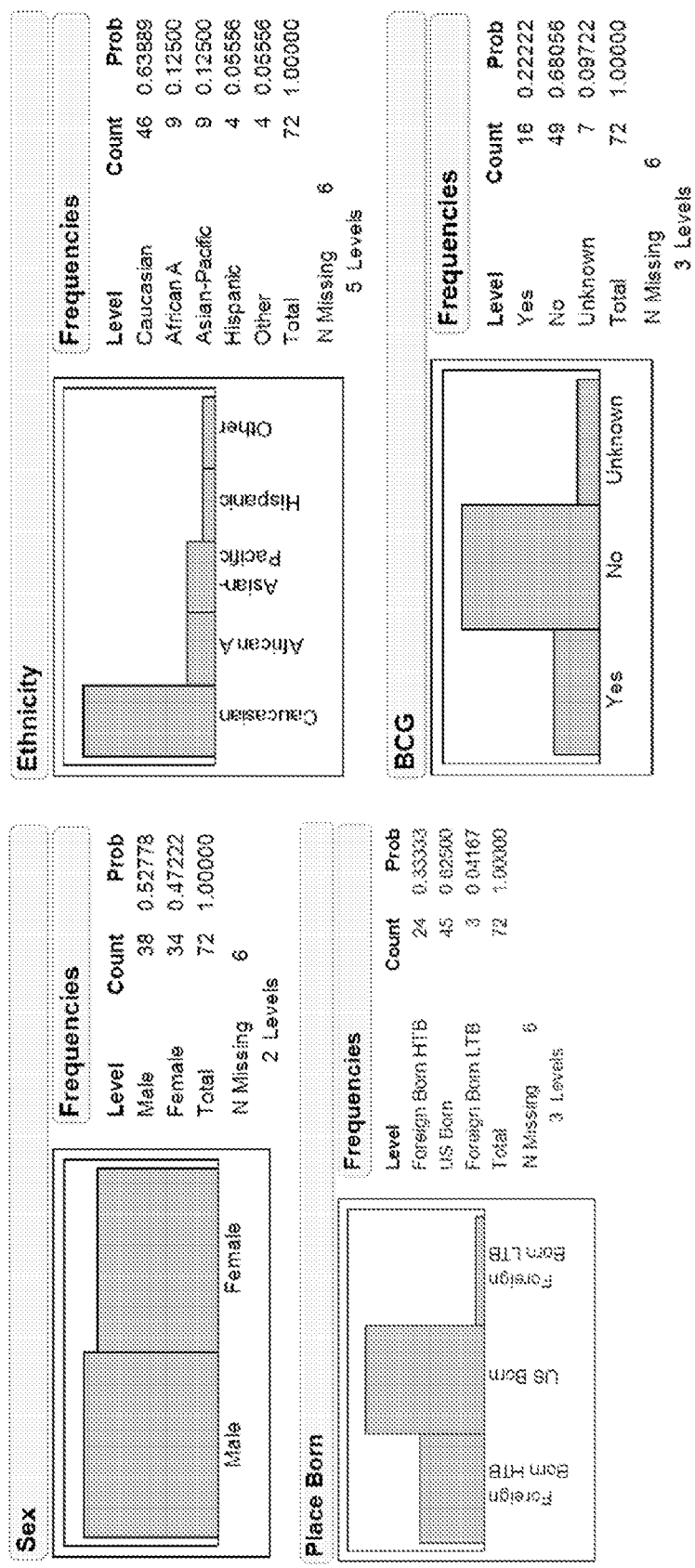
Figure 23:
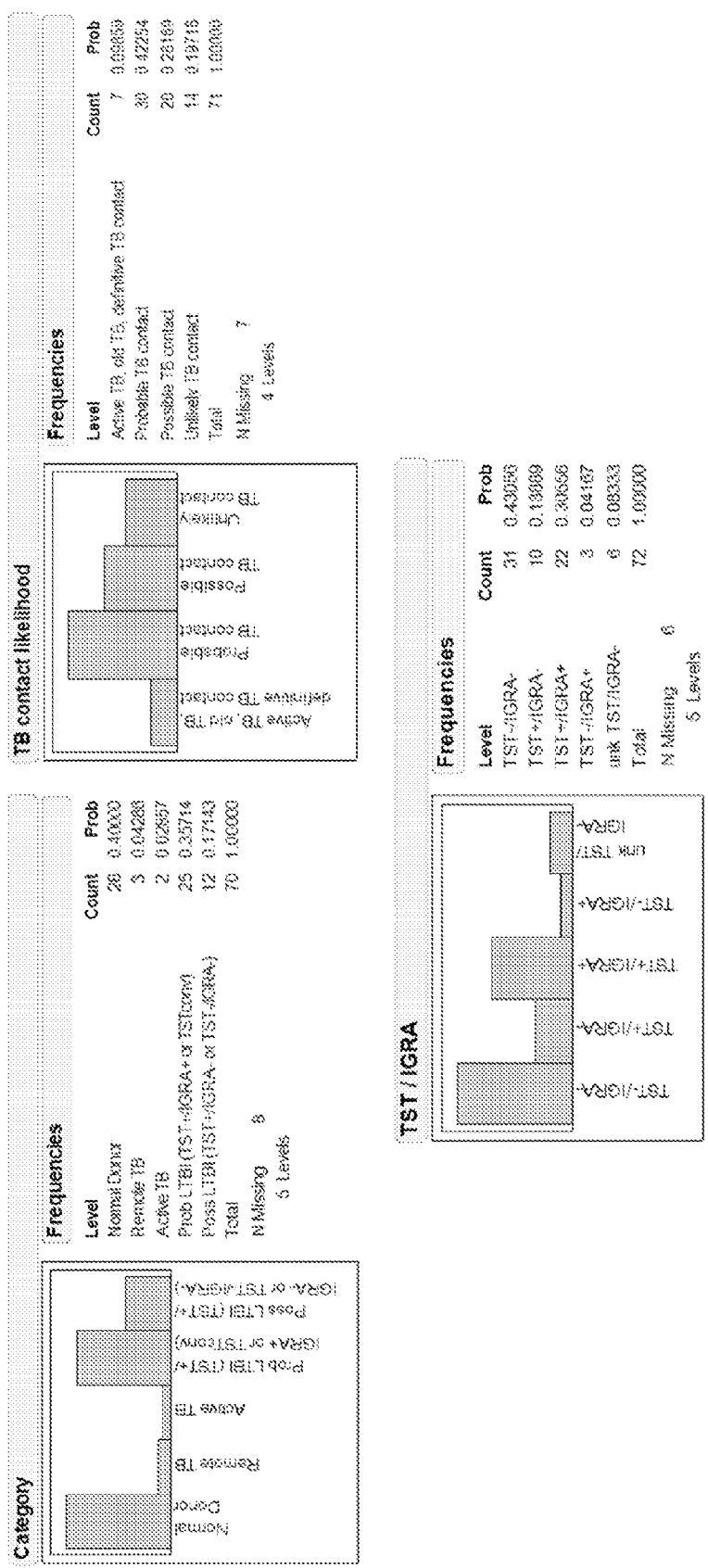
FIG. 23 provides clinical characteristics (N=72).
Figure 24:
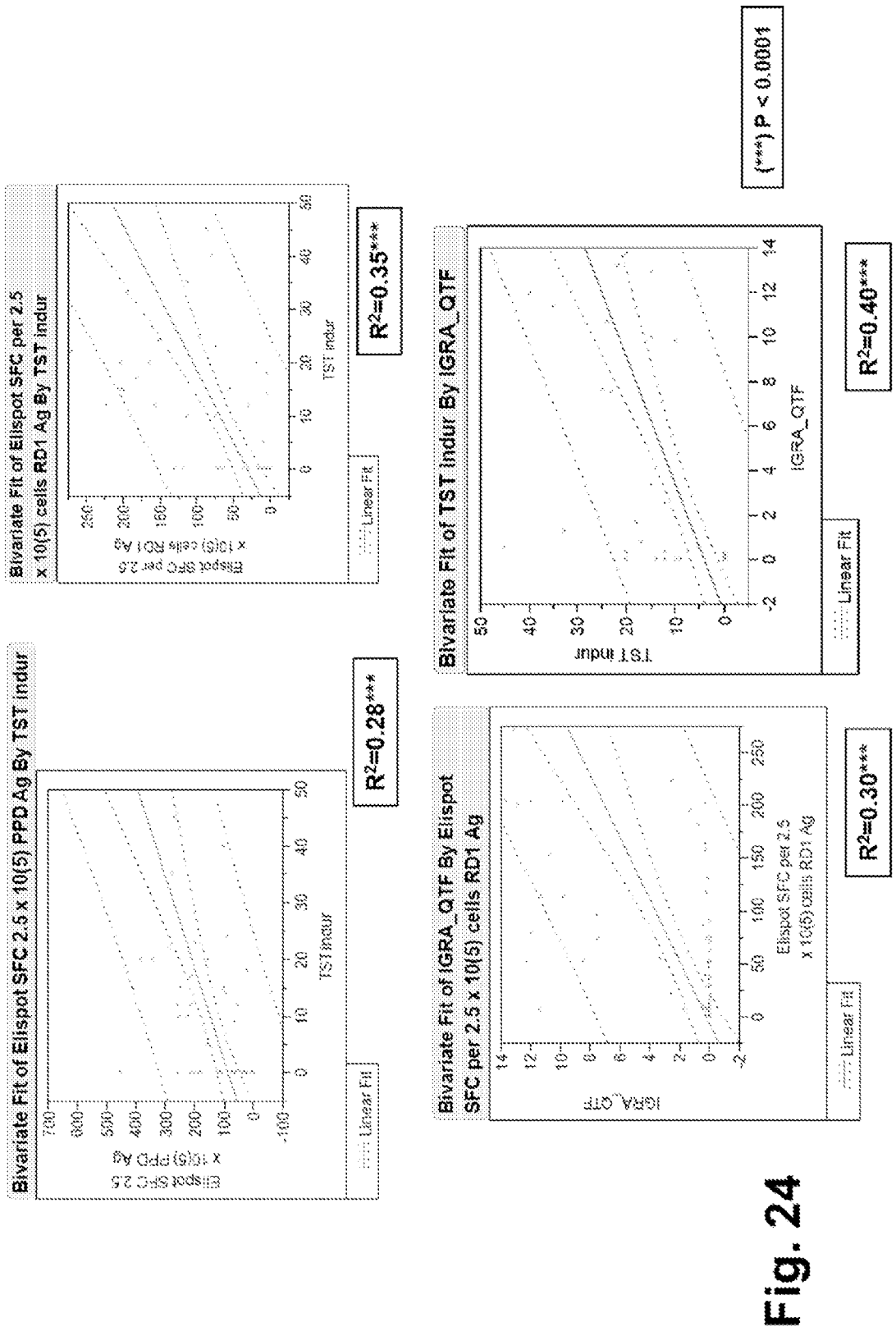
FIG. 24 contains graphs of TB-ELISPOT vs. QFT (QuantiFERON TB Gold IT™) and other correlations.
Figure 25:
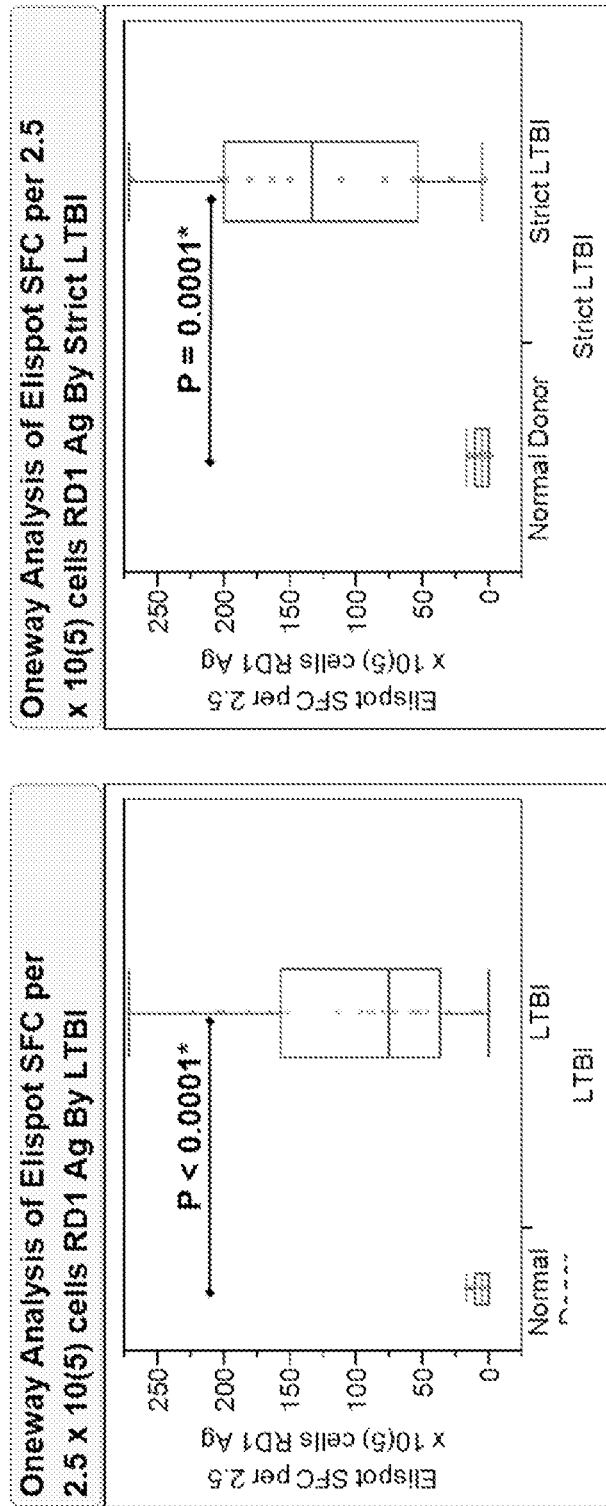
FIG. 25 contains graphs of TB-ELISPOT (RD1) for healthy donors vs. LTBI.
Figure 26:
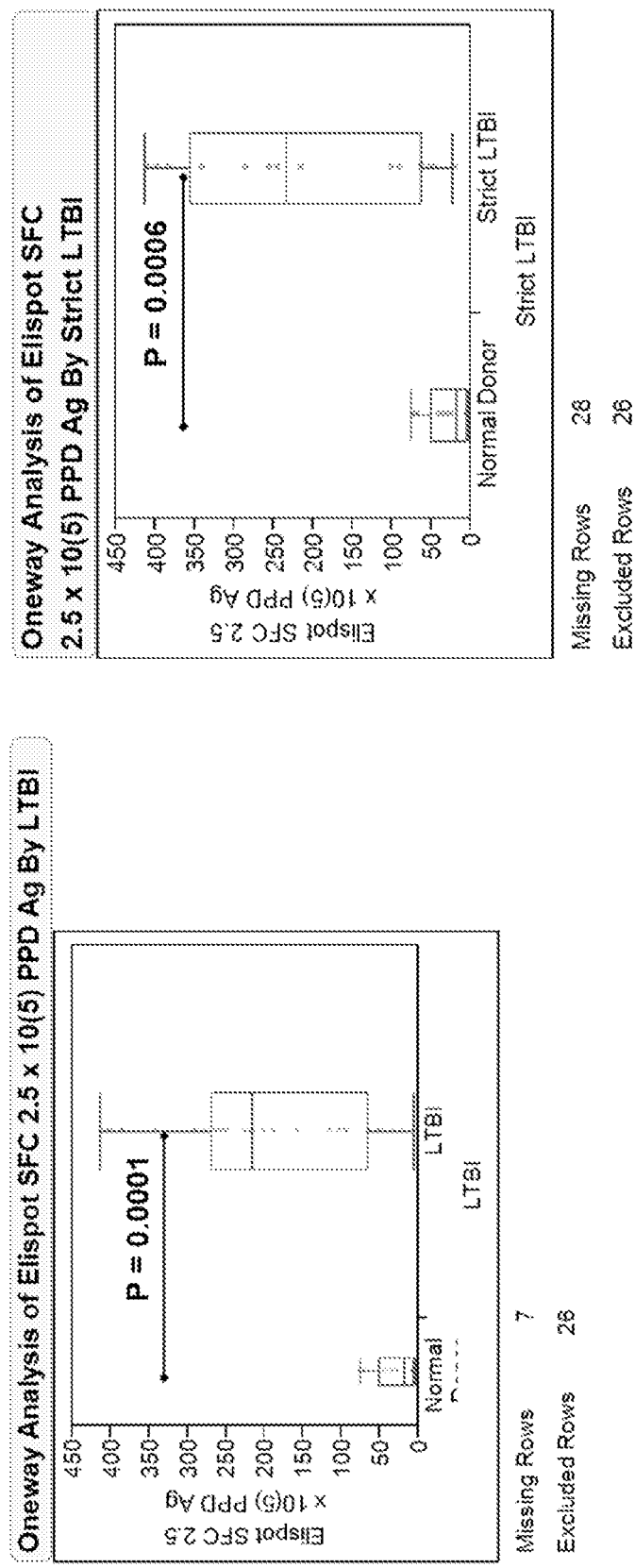
FIG. 26 contains graphs of TB-ELISPOT (PPD) for healthy donors vs. LTBI.
Figure 27:
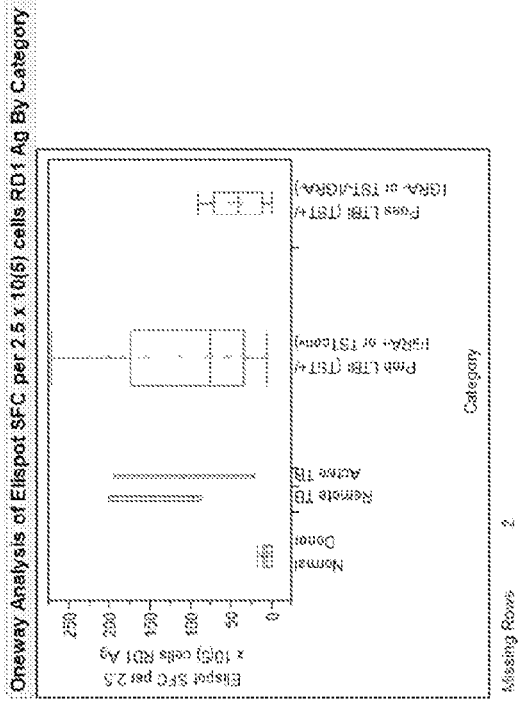
FIG. 27 contains graphs and table information of TB-ELISPOT (RD1).
Figure 27:
Figure 27:
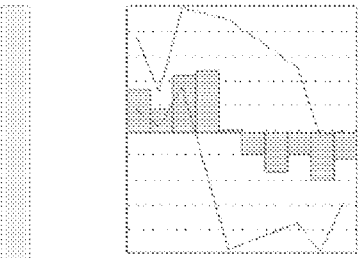
Figure 28:
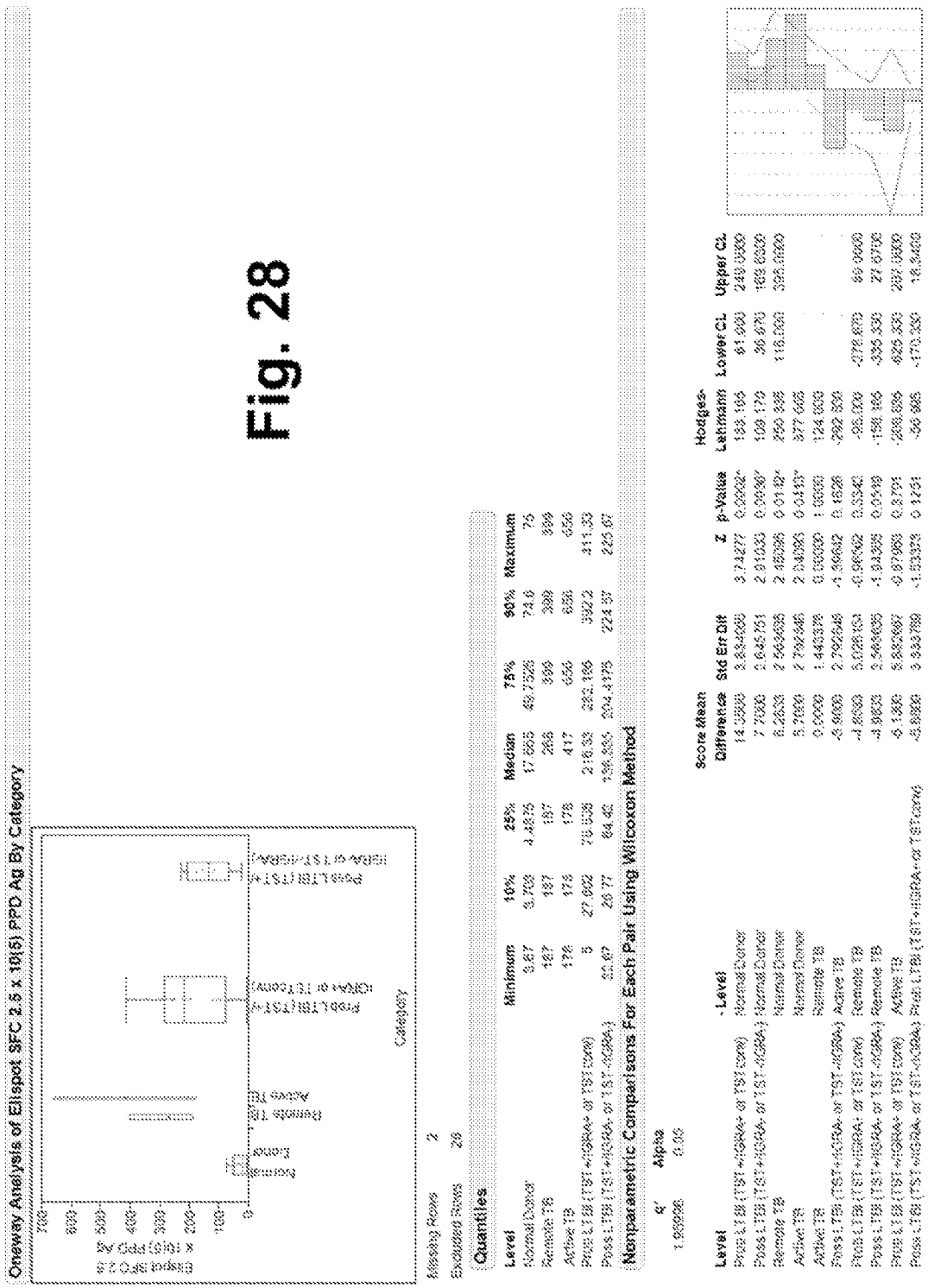
FIG. 28 contains graphs and table information of TB-ELISPOT (PPD).
Figure 29:
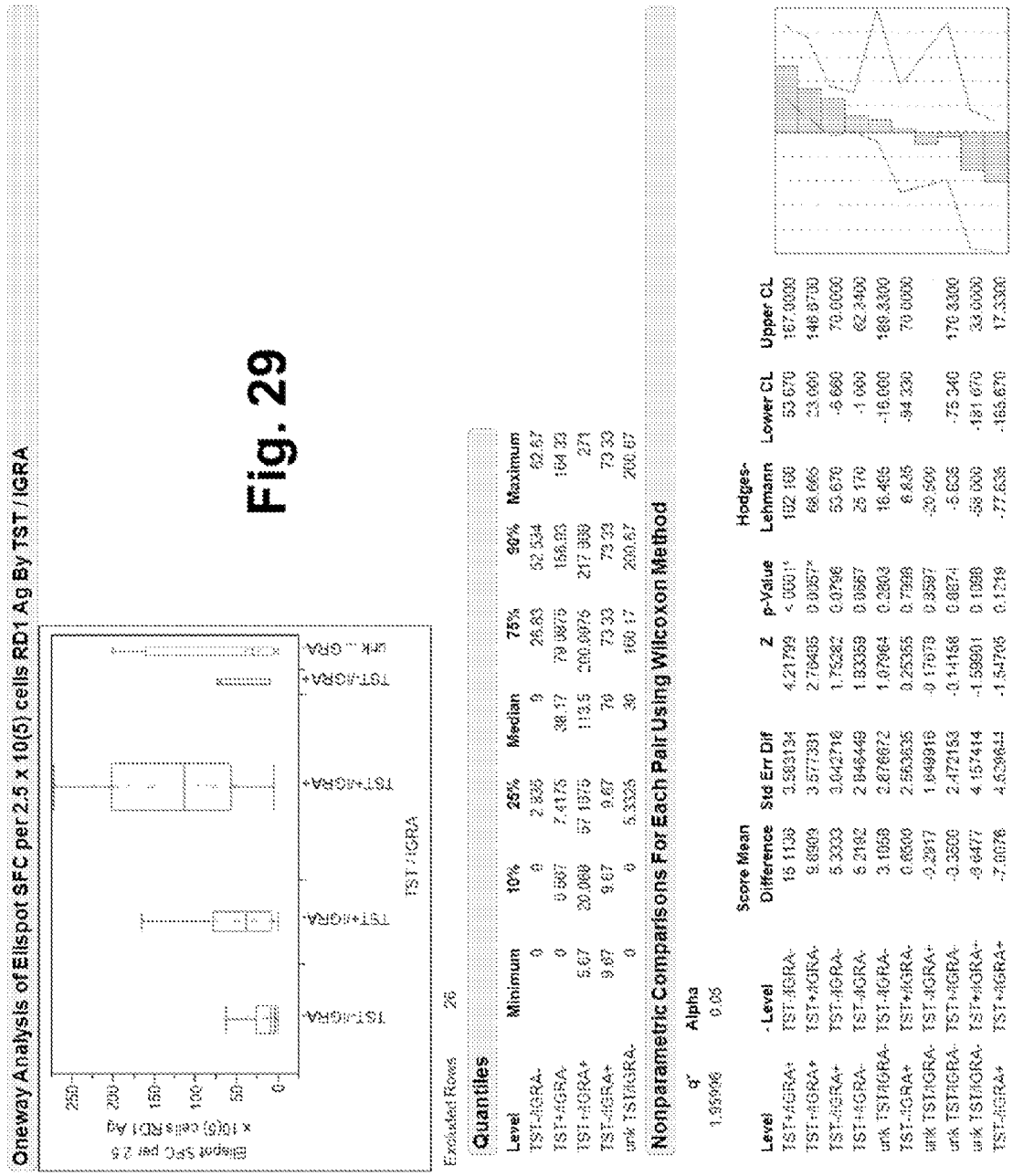
FIG. 29 contains graphs of ELISPOT-TB (RD1) by TST/IGRA results.
Figure 30:
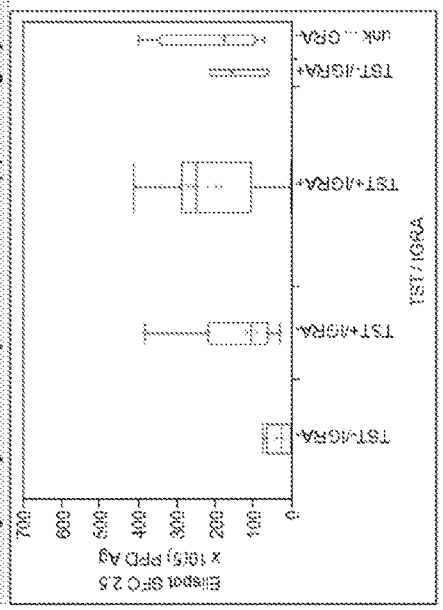
FIG. 30 contains graphs of ELISPOT-TB (PPD) by TST/IGRA results.
Figure 30:
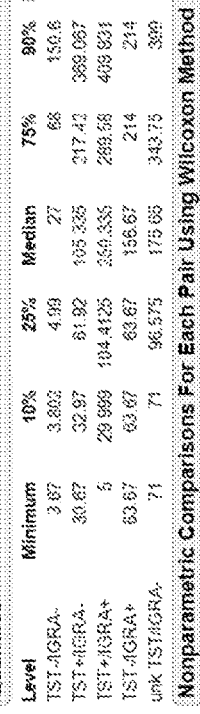
Figure 30:
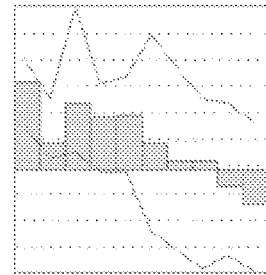
Figure 31:
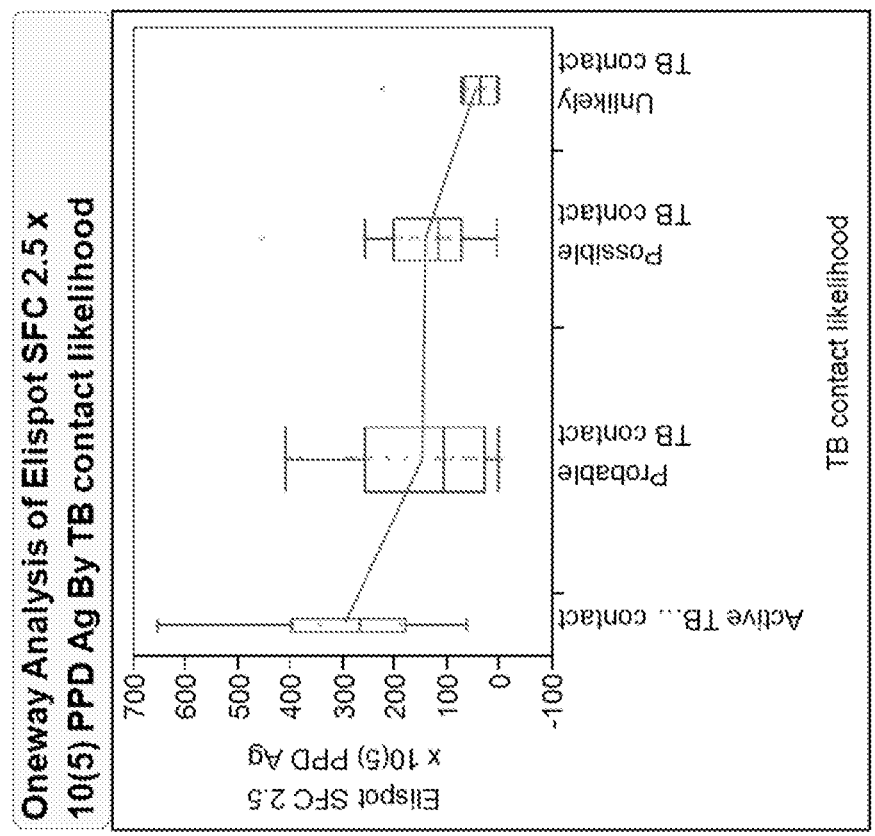
FIG. 31 contains graphs of ELISPOT-TB (RD1 vs. PPD) by TB contact likelihood.
Figure 31:
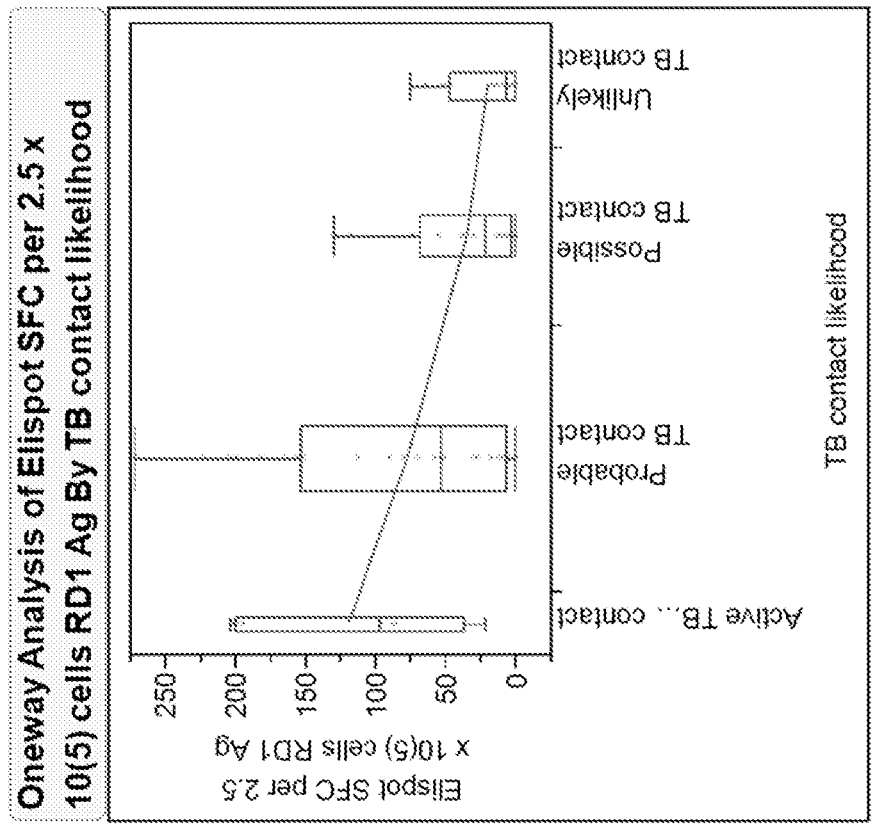
Figure 32:
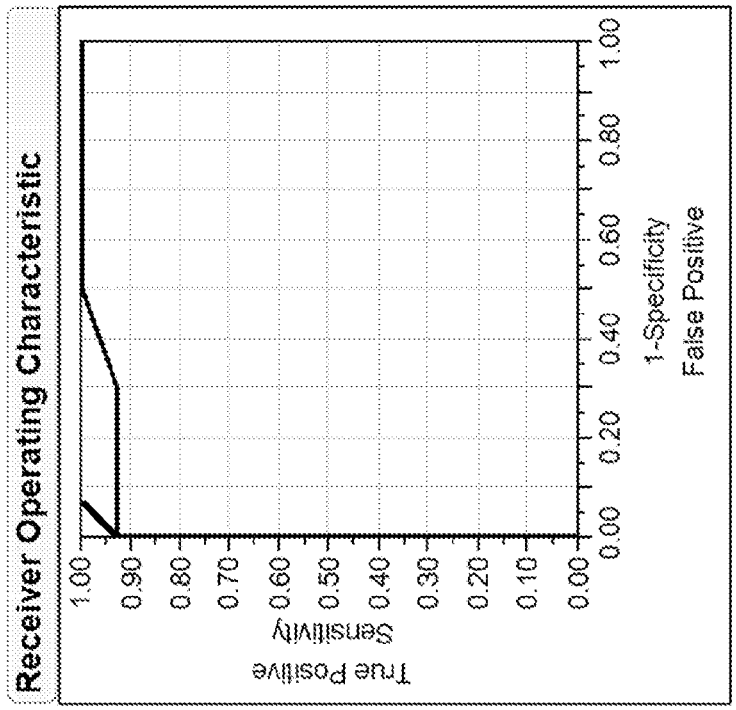
FIG. 32 contains graphs of TB-ELISPOT (RD1): ROC results for LTBI vs. LTBI strict definition.
Figure 32:
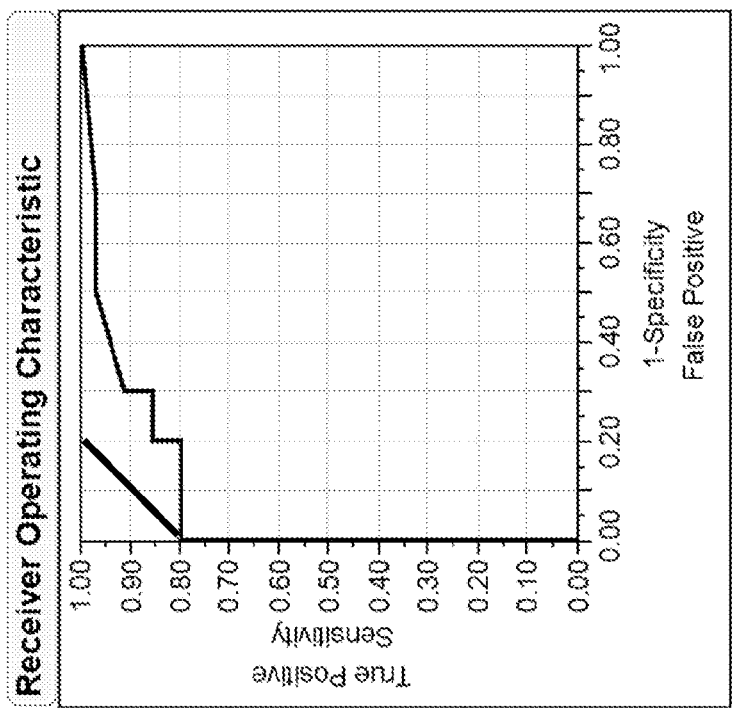
Figure 33:
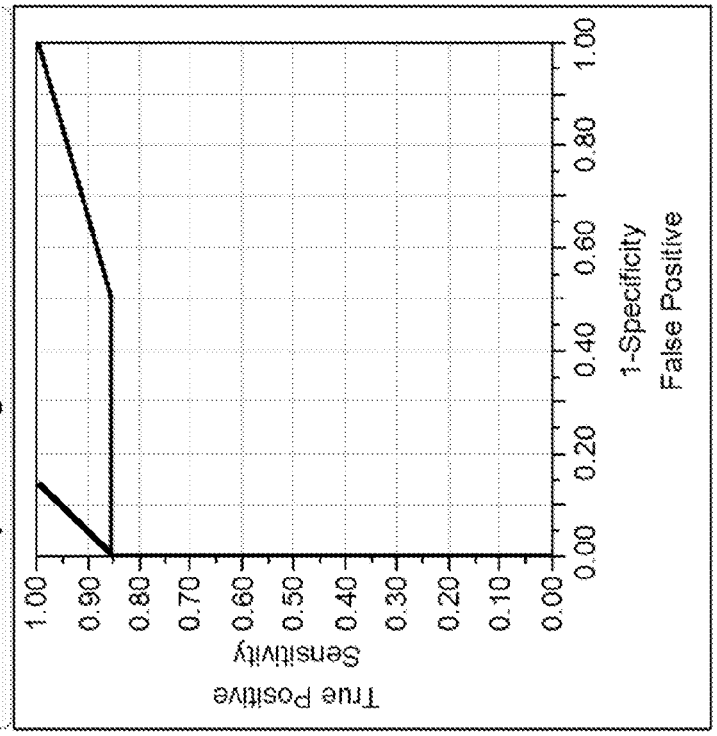
FIG. 33 contains graphs of QuantiFERON TB Gold In-Tube™: ROC results for LTBI vs. LTBI strict definition.
Figure 33:
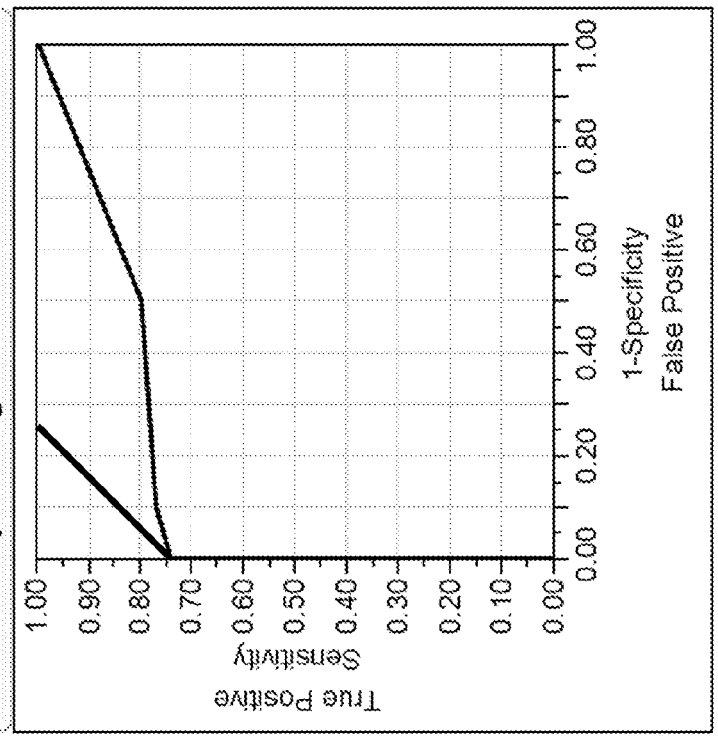
Figure 34:
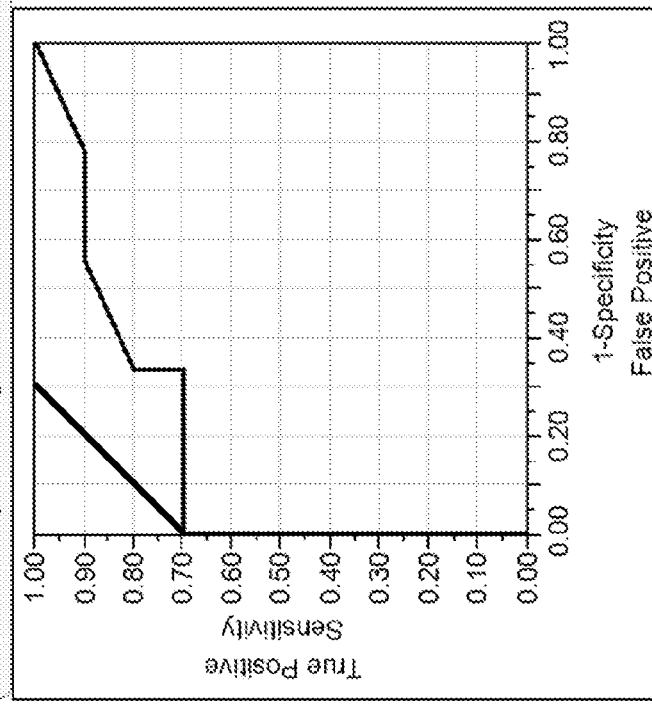
FIG. 34 contains graphs of TB-ELISPOT (RD1): ROC results for TST+/IGRA+vs. TST+/IGRA−.
Figure 34:
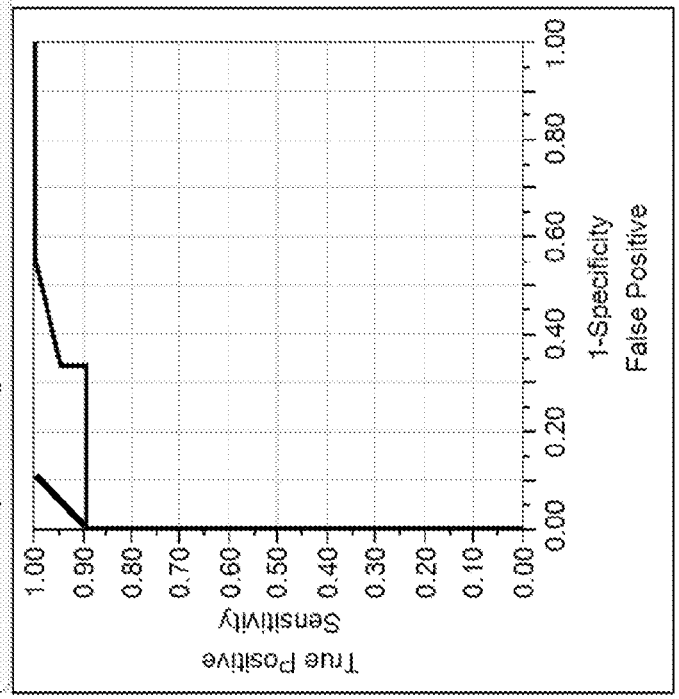
Figure 35:
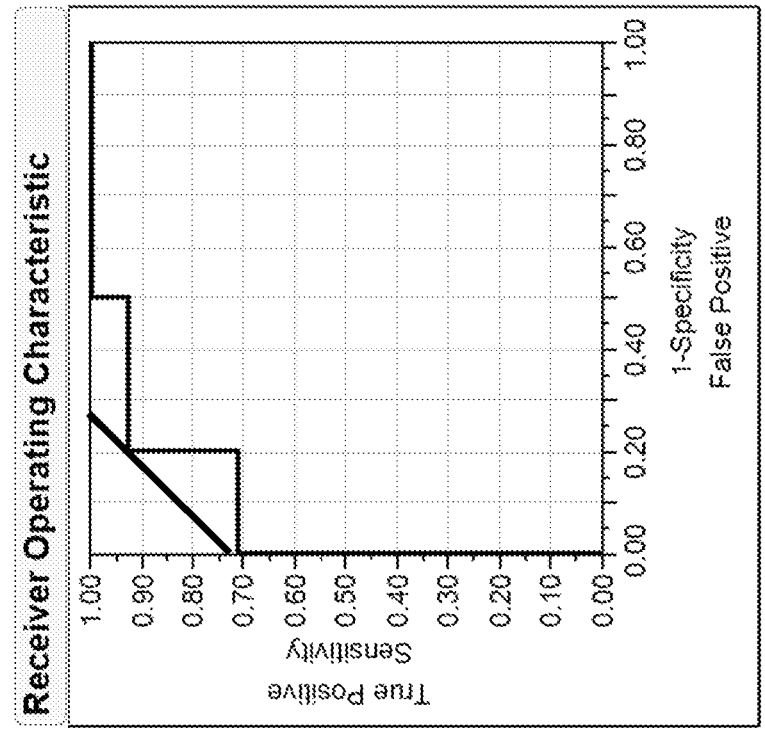
FIG. 35 contains graphs of TB-ELISPOT (PPD): ROC results for LTBI vs. LTBI strict definition.
Figure 35:
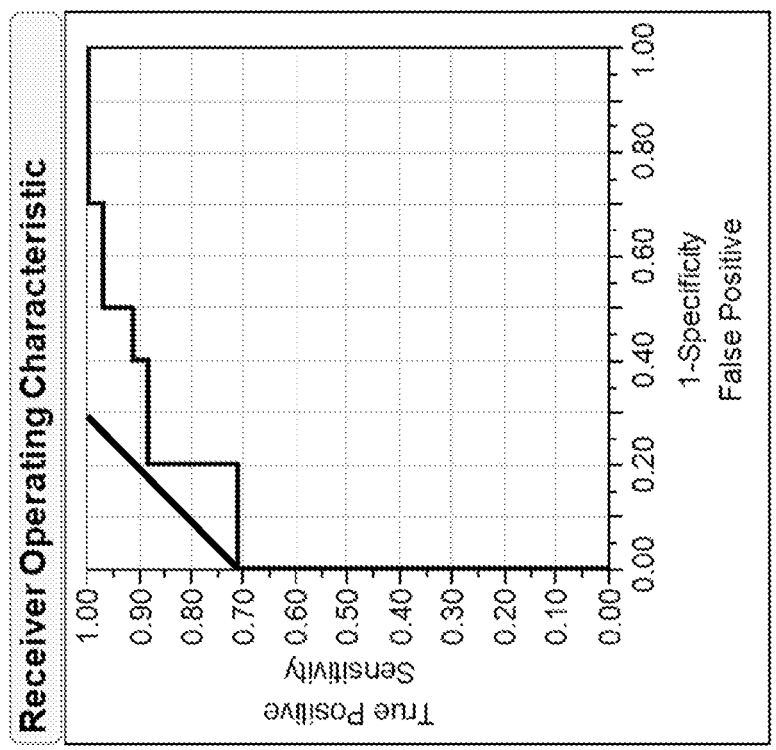
Figure 36:
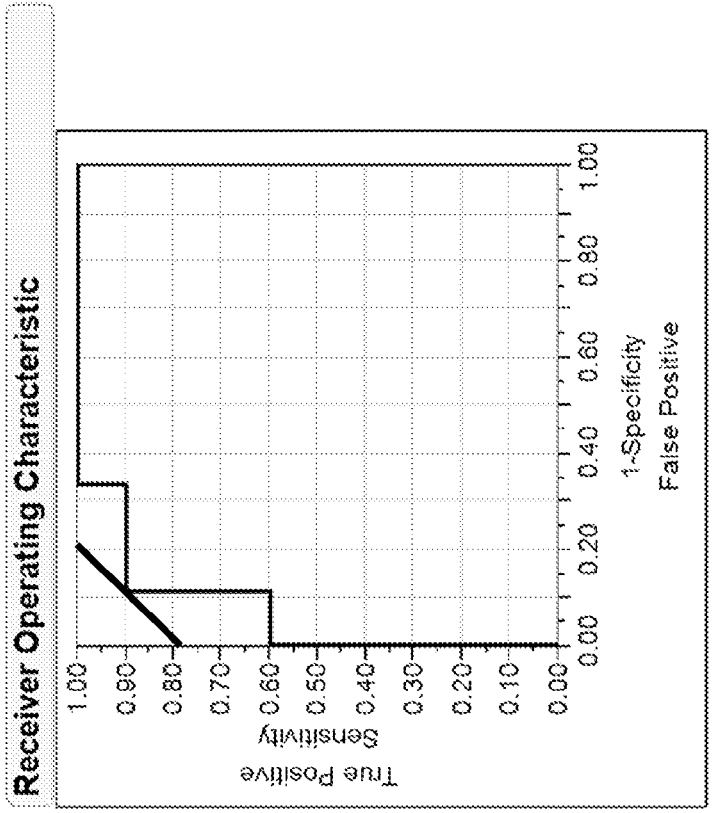
FIG. 36 contains graphs of TB-ELISPOT (PPD): ROC results for TST+/IGRA+vs. TST+/IGRA−.
Figure 36:
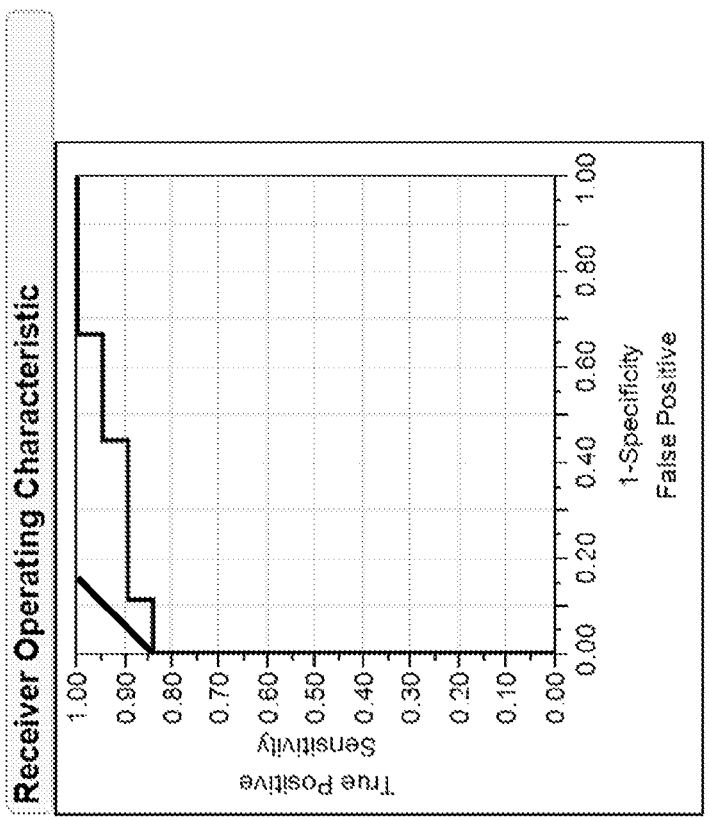
Figure 37:
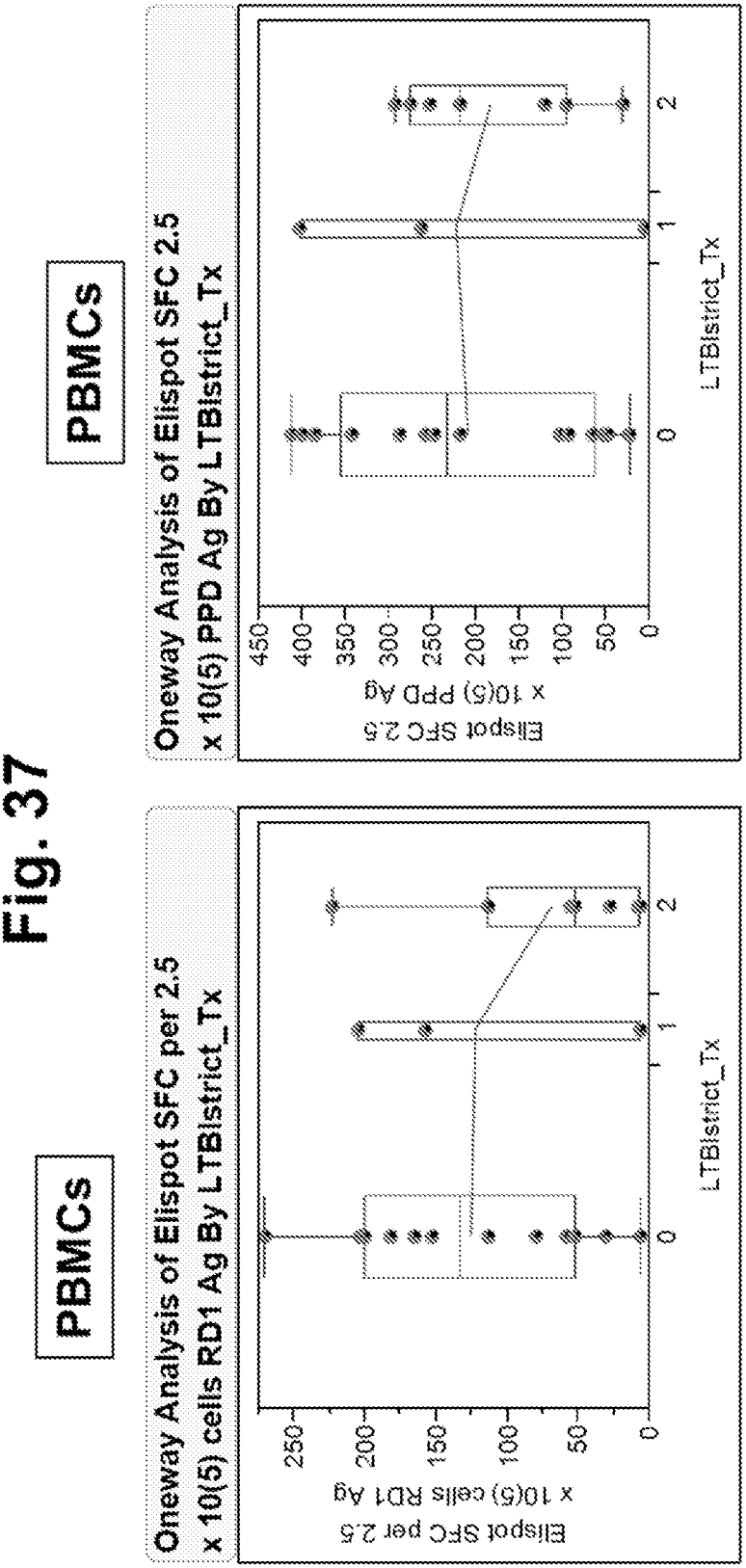
FIG. 37 contains results of an ELISPOT-TB (RD1 vs. PPD) in an analysis of samples from patients prior to (0), undergoing (1), and after (2) LTBI treatment.
Figure 38:
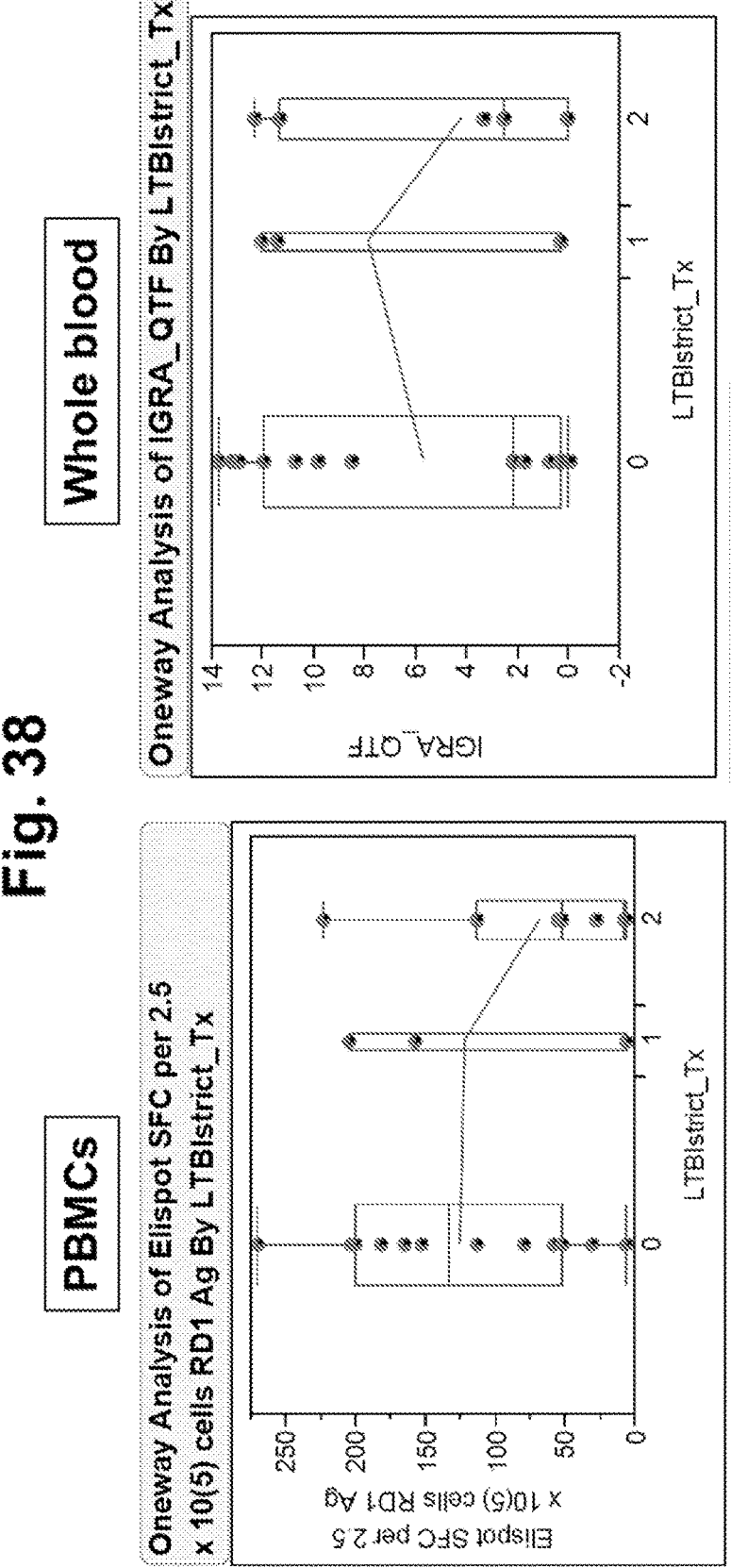
FIG. 38 contains a comparison of ELISPOT-TB (RD1) vs. QuantiFERON TB Gold In-Tube™ results from patients prior (0), undergoing (1), and after (2) LTBI treatment.

The diagnostic performance of TB-ELISPOT was compared with simultaneous commercial IGRA in a patient population with low, intermediate, and high risk of LTBI, and with either discordant or concordant previous TST/IGRA results (FIG. 18). TB-ELISPOT accurately differentiated normal donors from highly suspected LTBI cases, including some cases with TST-pos/IGRA-neg results. TB-ELISPOT exhibited a higher rate of detection of antigen-specific T-cell activation to RD1 antigens compared with commercial IGRA, which can allow for a more accurate detection of LTBI in patients with discordant TST-pos/IGRA-neg results. Additional results are provided in FIGS. 19-38.

These results demonstrate that an enhanced ELISpot technique for TB can be performed with a high diagnostic yield. TB-ELISPOT detected some false negative IGRA results. These results also demonstrate that false negative TB-ELISPOT results can occur with immunosuppression. In addition, these results demonstrate that TB-ELISPOT with RD1 and PPD can accurately differentiate LTBI versus healthy controls. TB-ELISPOT (with RD1 more than PPD) appeared to detect LTBI in TST-pos/IGRA-neg cases. TB-ELISPOT (RD1) appeared to have the highest diagnostic performance for LTBI with either TST-pos/IGRA-pos or TST-pos/IGRA-neg cases.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit for detecting a latent tuberculosis infection comprising an anti-CD28 antibody, an anti-CD49d antibody, a polypeptide mixture consisting of SEQ ID NO: 1, SEQ ID NO:2, SEQ ID NO:3, SEQ ID NO:4, SEQ ID NO:5 and SEQ ID NO:6 for stimulating cells, an enzyme-linked immunosorbent spot (ELspot) plate coated with an anti-interferon-γ capture antibody; and an anti-interferon-γ detection antibody for identifying a number of cells having the ability to release interferon-γ.

* * * * *

UNITED STATES PATENT AND TRADEMARK OFFICE
CERTIFICATE OF CORRECTION

PATENT NO. : 9,678,071 B2  
APPLICATION NO. : 14/371371  
DATED : June 13, 2017  
INVENTOR(S) : Patricio Escalante, Keith L. Knutson and Tobias Peikert Page 1 of 1

It is certified that error appears in the above-identified patent and that said Letters Patent is hereby corrected as shown below:

On the Title Page

Column 2 (Other Publications), please delete "6" and insert -- 18 --, therefor;

In the Specification

Column 1, Line 8, after "U.S.C." insert -- § --, therefor;

In the Claims

Column 11, Line 33 (Claim 1), please delete "NO: 1," and insert -- NO:1, --, therefor;

Column 12, Line 30 (Claim 1), please delete "(ELspot)" and insert -- (ELISpot) --, therefor.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*